US006159890A

United States Patent [19]
Nubel et al.

[11] Patent Number: 6,159,890
[45] Date of Patent: *Dec. 12, 2000

[54] RUTHENIUM-CONTAINING CATALYST SYSTEM FOR OLEFIN METATHESIS

[75] Inventors: Philip O. Nubel; Craig Lane Hunt; David S. Choi, all of Naperville; Tobin J. Marks, Evanston, all of Ill.

[73] Assignee: BP Amoco Corporation, Chicago, Ill.

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 09/181,352

[22] Filed: Oct. 28, 1998

Related U.S. Application Data

[63] Continuation-in-part of application No. 08/842,251, Apr. 24, 1997.
[60] Provisional application No. 60/068,347, Dec. 19, 1997, provisional application No. 60/064,508, Nov. 5, 1997, provisional application No. 60/016,554, Apr. 30, 1996, and provisional application No. 60/033,257, Dec. 6, 1996.

[51] Int. Cl.$^7$ .................................................. B01J 31/00

[52] U.S. Cl. ......................... 502/155; 502/158; 502/172; 502/169; 502/156

[58] Field of Search ................................... 502/150, 152, 502/155, 156, 158, 161, 169, 170, 172, 162

[56] References Cited

U.S. PATENT DOCUMENTS

| | | | |
|---|---|---|---|
| 3,117,952 | 1/1964 | Meriwether | 260/94.1 |
| 3,597,403 | 8/1971 | Ofstead | 260/88.2 |
| 3,798,175 | 3/1974 | Streck et al. | 252/429 |
| 3,855,323 | 12/1974 | Lyons | 260/666 A |
| 3,857,825 | 12/1974 | Streck et al. | 260/88.1 |
| 3,957,827 | 5/1976 | Lyons | 502/155 |
| 3,962,294 | 6/1976 | Lyons | 502/155 |
| 4,323,508 | 4/1982 | Herrington et al. | 260/346.11 |
| 5,312,940 | 5/1994 | Grubbs et al. | 556/136 |
| 5,324,616 | 6/1994 | Sacripante et al. | 430/137 |
| 5,342,909 | 8/1994 | Grubbs et al. | 526/171 |
| 5,405,924 | 4/1995 | Kelsey | 526/142 |
| 5,491,206 | 2/1996 | Brown-Wensley et al. | 526/126 |
| 5,559,262 | 9/1996 | Beatty et al. | 502/155 |
| 5,599,962 | 2/1997 | Beatty et al. | 556/21 |
| 5,710,298 | 1/1998 | Grubbs et al. | 502/155 |
| 5,726,334 | 3/1998 | Beatty et al. | 502/155 |
| 5,728,785 | 3/1998 | Grubbs et al. | 526/142 |
| 5,728,917 | 3/1998 | Grubbs et al. | 585/653 |
| 5,750,815 | 5/1998 | Grubbs et al. | 585/511 |
| 5,831,108 | 11/1998 | Grubbs et al. | 502/152 |
| 5,849,851 | 12/1998 | Grubbs et al. | 526/93 |

(List continued on next page.)

FOREIGN PATENT DOCUMENTS

| | | |
|---|---|---|
| 0 366 390 | 5/1990 | European Pat. Off. . |
| 0839821 | 5/1998 | European Pat. Off. . |
| WO 91/02588 | 3/1991 | WIPO . |
| WO 92/15400 | 9/1992 | WIPO . |
| WO 96/16100 | 5/1996 | WIPO . |
| WO 96/20235 | 7/1996 | WIPO . |
| 9740934 | 11/1997 | WIPO . |
| 9839346 | 9/1998 | WIPO . |

OTHER PUBLICATIONS

C. Grunwald et al., Advance ACS Abstracts, vol. 4, No. 6, p. 140, Mar. 15, 1996.

Gruenwald, C., et al., "Five–Coordinate 16–Electron Carbene–and Vinylideneruthenium (II) Complexes Prepared from [RuCl2(C8H12)]n or from the New Dihydridoruthenium (IV) Compound [RuH2Cl2(PiPr3)2]", Organometallics (1996), 15: 1960–1962.

Demonceau, A., et al., Novel Ruthenium–Based Catalyst Systems for the Ring–Opening Metathesis Polymerization of Low–Strain Cyclic Olefins, Macromolecules (1997), 30: 3127–3136.

K.J. Ivin, "Summary of Catalyst Systems", Olefin Metathesis, Academic Press, New York, 1983, p. 34.

Porri, L., et al., "Ring–Opening Polymerization of Cycloolefins with Catalysts Derived from Ruthenium and Iridiuim", Die Makromolekulare Chemie, 1974, 175: 3097–3115.

Demonceau, A., et al., "Ruthenium–catalysed ring–opening metathesis polymerization of cycloolefins initiated by diazoesters", J. Mol. Catal, 1992, 76: 123–132.

Stumpf, A.W., et al., "Ruthenium–based Catalysts for the Ring Opening Metathesis Polymerization of Low–strain Cyclic Olefins and of Functionalised Derivatives of Norbornene and Cyclooctene", J. Chem. Soc., Chem. Commun., 1995, pp. 1127–1128.

Schwab, P., et al., A "Series of Well–Defined Metathesis Catalysts—Synthesis of [RuCl2(=CHR') (PR3)2] and Its Reactions", Angew. Chem. Int. Ed. Engl., 1995, 34: 2039–2041.

Schwab, P., et al., "Synthesis and Applications of RuCl2(=CHR')(PR3)2: The Influence of the Alkylidene Moiety on Metathesis Activity", J. Am. Chem. Soc., 1996, 118: 100–110.

Creary, X., "Tosylhydrazone Salt Pyrolyses: Phenyldiazomethanes", Org. Synth., Coll. vol. 7, 1990, pp. 438–443.

Primary Examiner—Mark L. Bell
Assistant Examiner—J. Pasterczyk
Attorney, Agent, or Firm—James R. Henes; Wallace L. Oliver

[57] ABSTRACT

A ruthenium-containing metathesis catalyst system which contains a ruthenium compound (A), a phosphorus, arsenic, or antimony compound (B), and a compound (C) containing at least one carbon-to-carbon triple bond. The mole ratio of compounds A:B:C is typically in the range of about 1.0:0.01–100:0.01–500. The ruthenium compound (A) is a Ru(II), Ru(III), or Ru(IV) compound containing an anionic ligand (X) and optionally an arene ligand and optionally a phosphorus, arsenic, or antimony compound ligand. The compound (B) is optional if the ruthenium compound (A) contains a phosphorus-, arsenic-, or antimony-containing ligand. Hydrogen gas is used as an activator. A process for metathesis of olefins involves reacting at least one olefin with the catalyst system described herein.

8 Claims, No Drawings

U.S. PATENT DOCUMENTS

| | | | |
|---|---|---|---|
| 5,880,231 | 3/1999 | Grubbs et al. | 526/171 |
| 5,900,521 | 5/1999 | Park et al. | 502/161 |
| 5,912,376 | 6/1999 | Van Der Schaaf et al. | 502/155 |
| 5,917,071 | 6/1999 | Grubbs et al. | 502/152 |
| 5,919,962 | 7/1999 | Sayo et al. | 502/162 |
| 5,929,289 | 7/1999 | Abatjoglou et al. | 502/158 |
| 5,939,504 | 8/1999 | Woodson, Jr. et al. | 502/155 |
| 5,977,393 | 11/1999 | Grubbs et al. | 502/162 |
| 5,981,421 | 11/1999 | Paez et al. | 502/155 |
| 5,998,326 | 12/1999 | Hafner et al. | 502/155 |
| 6,048,993 | 8/1999 | Grubbs et al. | 502/162 |

RUTHENIUM-CONTAINING CATALYST SYSTEM FOR OLEFIN METATHESIS

REFERENCE TO RELATED APPLICATIONS

This application claims the benefit of the filing dates of U.S. Provisional Application Ser. No. 60/068,347, filed Dec. 19, 1997 and U.S. Provisional Application Ser. No. 60/064, 508, filed Nov. 5, 1997, and is a continuation-in-part of U.S. patent application Ser. No. 08/842,251, filed Apr. 24, 1997, which in turn claims the benefit of the filing dates of U.S. Provisional Application Ser. No. 60/016,554, filed Apr. 30, 1996, and U.S. Provisional Application Ser. No. 60/033,257, filed Dec. 6, 1996, all of which are incorporated herein by reference in their entirety.

BACKGROUND OF THE INVENTION

1. Field of the Invention

This invention is directed to a ruthenium-containing catalyst system for olefin metathesis and to a catalytic olefin metathesis process employing the ruthenium-containing catalyst system.

2. Discussion of the Prior Art

Conventional ring-opening olefin metathesis polymerization (ROMP) is the catalyzed reaction of a cyclic olefin monomer to yield an unsaturated polymer:

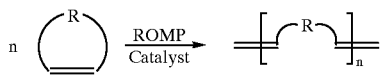

Procedures to prepare polymeric hydrocarbons having reactive functional endgroups have used cyclic olefinic compounds in conjunction with a ring opening step. Ofstead, U.S. Pat. No. 3,597,403, teaches a process for ring-opening polymerization of unsaturated alicyclic compounds, preferably unsaturated alicyclic compounds of a single unsaturated alicyclic ring, in the presence of a catalyst system comprising an alkylaluminum halide, molecular oxygen, and a compound of tungsten or molybdenum; generally the single unsaturated alicyclic ring contains at least four carbon atoms and not more than five carbon atoms wherein the carbon-to-carbon double bonds in the ring are not adjacent and are non-conjugated. Streck et al., U.S. Pat. No. 3,798,175, teaches a process for ring opening polymerization of cyclic olefins and forming terminal carbalkoxy groups by employing a catalyst system consisting essentially of (1) a tungsten or molybdenum compound, (2) an organo aluminum compound, and (3) an unsaturated carboxylic acid ester. Streck et al,. U.S. Pat. No. 3,857,825, discloses a process for production of polymeric hydrocarbons having reactive silyl end groups by a ring-opening polymerization of a cyclic olefin in the presence of a catalytic amount of a halogenated compound of a metal selected from the group consisting of niobium, tantalum, molybdenum, tungsten and rhenium, and a halogen, alkoxy, carboxylate or Lewis acid.

Ruthenium-based catalysts for olefin metathesis have become of interest because they are able to effect the metathesis of certain types of olefins containing functional groups (e.g., hydroxyl, carboxylic acid, or ester groups), unlike many metathesis catalysts based on other metals such as molybdenum, tungsten, or rhenium. However, most ruthenium-based catalysts only can effect metathesis of highly strained cyclic olefins such as norbornene and norbornene derivatives, cyclobutene and cyclobutene derivatives, and dicyclopentadiene, and are unable to metathesize less strained cyclic olefins or acyclic olefins (K. J. Ivin, Olefin Metathesis, Academic Press, New York, 1983, p. 34). For example, $RuCl_3$ catalyzes the ring-opening metathesis polymerization (ROMP) of norbornene but not olefins with significantly lower ring strain such as cyclopentene, cyclooctene, or 1,5-cyclooctadiene. L. Porri et al., Die Makromolekulare Chemie, 1974, 175: 3077–3115, reported two ruthenium compounds [dichloro(2,7-dimethylocta-2,6-diene-1,8-diyl)ruthenium and bis (trifluoroacetato)-2,7-dimethlyocta-2,6-diene-1,8-diyl) ruthenium] that are able to cause slow metathesis of cyclopentene after treatment with hydrogen, but these systems were not able to effect metathesis of cyclooctene or acyclic olefins.

More recently, A. Demonceau, et al., J. Mol. Catal., 1992, 76: 123–132; A. W. Stumpf, et al., J Chem. Soc., Chem. Commun., 1995, pages 1127–1128 and A. Demonceau, et al., Macromolecules, 1997, 30:3127–3136, reported a catalyst system which was able to effect ring opening metathesis polymerization (ROMP) of cyclooctenes. This catalyst system consists of (1) an $[RuCl_2(arene)]_2$ complex combined with a phosphine (tricyclohexyl- or triisopropyl-phosphine) and (2) an organic diazo compound such as trimethylsilyidiazomethane or ethyl diazoacetate. Also, P. Schwab et al., Angew. Chem. Int. Ed. Engl., 1995, 34: 2039–2041; P. Schwab, et al., J Am. Chem. Soc., 1996, 118: 100–110, reported a one-component ruthenium complex of the general formula $RuCl_2(PR_3)_2(=CHR')$ that is able to catalyze metathesis of acyclic olefins and low-strain cyclic olefins. The catalyst reported in these two references is most active with bulky phosphine ligands such as tricyclohexyl- or triisopropyl-phospine. This one-component ruthenium complex catalyst has been prepared by several different synthetic routes, including reaction of ruthenium complexes with organic diazo compounds (P. Schwab et al., Angew. Chem. Int. Ed. Engl., 1995, 34: 2039–2041; P. Schwab, et al., J Am. Chem. Soc., 1996, 118: 100–110), with acetylene or 1-alkynes (C. Grunwald, et al., Organometallics, 1996, 15: 1960–1962; J. Wolf, et al., Angew. Chem. Int Ed., 1998, 37: 1124–1126), with propargyl and vinyl chlorides (T. E. Wilhelm, et al., Organometallics, 1997, 16: 3867–3869), and with organic dihalo compounds (T. R. Belderrain et al., Organometallics, 1997, 16: 4001–4003; M. Olivan et al., Chem. Commun., 1997, pages 1733–1734). Also, Furstner et al., Chem. Commun., 1998, pages 1315–1316, reported an effective metathesis catalyst, $[Ru(=C=C=CR_2)(PR_3)Cl (arene)]PF_6$, prepared by the reaction of $RuCl_2L(arene)$, prop-2-yn-1-ol, and $NaPF_6$.

The catalysts reported by P. Schwab et al. and by Furstner et al. are not convenient to utilize because they are not readily available and must be synthesized in multistep procedures. Some syntheses of the catalyst of P. Schwab et al. employ organic diazo compounds such as phenyldiazomethane that are expensive, not readily available commercially, and dangerously unstable, being known to explode even at room temperature (X. Creary, Org. Synth., Coll. Vol. 7, 1990, pages 438–443). The catalyst system reported by A. Demonceau et al. and A. W. Stumpf et al. utilizes an organic diazo compound as a catalyst component.

The present invention is a ruthenium-containing catalyst for olefin metathesis that is extremely convenient to utilize because no syntheses of ruthenium complexes are required. The catalyst components are readily available from commercial sources and are utilized directly in the olefin metathesis reaction. For example, simple ruthenium chloride or bromide can be employed as the ruthenium-containing component of the catalyst. Furthermore, no organic diazo compounds are employed, and the catalysts of the present invention have high activity and selectivity for metathesis of acyclic olefins and metathesis of low-strain cyclic olefins.

SUMMARY OF THE INVENTION

The present invention is a ruthenium-containing metathesis catalyst system which comprises (1) a ruthenium compound (A), (2) a phosphorus, arsenic or antimony compound (B), and (3) a compound (C) containing at least one carbon-to-carbon triple bond, wherein, the mole ratios of compounds A:B:C are in the range of about 1.0:0.01–100:0.01–500. The ruthenium compound (A) is a Ru(II), Ru(III), or Ru(IV) compound containing an anionic ligand (X), optionally an arene ligand and optionally a phosphorus, arsenic, or antimony compound ligand. The compound (B) is optional when the ruthenium compound (A) contains a phosphorus-, arsenic-, or antimony-containing ligand. The ruthenium compound (A) is selected from the group consisting of $[RuX_2(arene)]_2$, $RuX_2(arene)(ERR^1R^2)$, $RuX_2(arene)(EHRR^1)$, $RuX_2(arene)(EH_2R)$, $RuX_2(arene)[E(OR)(OR^1)(OR^2)]$, $RuX_3$, $RuX_3$ hydrate, $RuX_2(ERR^1R^2)_3$, $RuX_2(EHRR^1)_3$, $RuX_2(EH_2R)_3$, $RuX_2[E(OR)(OR^1)(OR^2)]_3$, $RuX_2(ERR^1R^2)_4$, $RuX_2(EHRR^1)_4$, $RuX_2(EH_2R)_4$, and $RuX_2[E(OR)(OR^1)(OR^2)]_4$, wherein E is phosphorus, arsenic or antimony, and wherein R,$R^1$ and $R^2$ are the same or different and are each selected from the group consisting of substituted and unsubstituted alkyl, cycloalkyl, aryl and arylalkyl groups of up to about 20 carbon atoms.

The present invention is also a catalytic process for ring-opening metathesis polymerization of cyclic olefins, metathesis of acyclic olefins, acyclic diene metathesis polymerization, cross-metathesis of cyclic and acyclic olefins, ring-closing metathesis, metathesis depolymerization of unsaturated polymers and metathesis of functionalized olefins, which comprises contacting at least one olefin with the ruthenium-containing catalyst system described above.

DETAILED DESCRIPTION OF THE INVENTION

The present invention provides a simple ruthenium-containing catalyst for metathesis of olefins, and does not employ an expensive or potentially dangerous diazo compound as a catalyst component or precursor. This invention relates to a ruthenium-containing catalyst system used in olefin metathesis, and to the olefin metathesis process obtained thereby. The catalyst system comprises (1) a ruthenium compound (A), (2) a phosphorus, arsenic, or antimony compound (B), and (3) a compound (C) containing at least one carbon-to-carbon triple bond. The ruthenium compounds (A) useful in this invention include, for example, Ru(II), Ru(III), and Ru(IV) compounds containing an anionic ligand (X), optionally an arene ligand and optionally a phosphorus, arsenic, or antimony compound ligand (e.g., phosphine or phosphite). The compound (B) is optional if the ruthenium compound (A) contains a phosphorus-, arsenic-, or antimony-containing ligand.

The ruthenium compounds (A) useful in the invention are, $RuX_2(arene)]_2$, $RuX_2(arene)(ERR^1R^2)$, $RuX_2(arene)(EHRR^1)$, $RuX_2(arene)(EH_2R)$, $RuX_2(arene)[E(OR)(OR^1)(OR^2)]$, $RuX_3$, $RuX_3$ hydrate, $RuX_2(ERR^1R^2)_3$, $RuX_2(EHRR^1)_3$, $RuX_2(EH_2R)_3$, $RuX_2[E(OR)(OR^1)(OR^2)]_3$, $RuX_2(ERR^1R^2)_4$, $RuX_2(EHRR^1)_4$, $RuX_2(EH_2R)_4$, or $RuX_2[E(OR)(OR^1)(OR^2)]_4$ where E is phosphorus, arsenic, or antimony and preferably is phosphorus (P). Preferred ruthenium compounds (A) include $RuCl_3$, $RuCl_3$ hydrate, $RuBr_3$, $RuBr_3$ hydrate, $[RuCl_2(p\text{-cymene})]_2$, $[RuCl_2(4\text{-tert-butyltoluene})]_2$, $[RuCl_2(1,3\text{-diisopropylbenzene})]_2$, $[RuCl_2(1,4\text{-diisopropylbenzene})]_2$, $[RuCl_2(1,3,5\text{-triisopropylbenzene})]_2$.

The R groups of the phosphorus, arsenic or antimony compound ligand of the ruthenium compound (A), e.g, R, $R^1$ and $R^2$ above, are the same or different and are each selected from the group consisting of alkyl, cycloalkyl, aryl, and alkylaryl groups, unsubstituted or substituted, each group of up to about 20 carbon atoms (preferably up to about 12 carbon atoms, more preferably up to about 8 carbon atoms, most preferably up to about 6 carbon atoms); the substituents may be halogen (F, Cl, Br, and I), alkyl or aryl moieties of up to about 20 carbon atoms (preferably up to about 12 carbon atoms, more preferably up to about 8 carbon atoms, most preferable up to about 6 carbon atoms).

X is an anionic ligand (a negatively charged moiety). X may be an aliphatic anionic ligand (negatively charged aliphatic moiety) containing up to about 20 carbon atoms, preferably up to about 12 carbon atoms, more preferably up to about 8 carbon atoms, most preferably up to about 6 carbon atoms such as methyl, ethyl, propyl, isopropyl, butyl, hexyl), or an aromatic anionic ligand (negatively charged aromatic moiety) containing up to 20 carbon atoms, preferably up to 12 carbon atoms, more preferably up to about 8 carbon atoms such as phenyl or benzyl. X also may be selected from negatively charged inorganic or organic groups such as halogens, hydroxides, or alkoxides ($OR^3$, where $R^3$ is selected from the group consisting of alkyl, cycloalkyl, aryl, and alkylaryl groups, each group of up to about 20 carbon atoms, preferably up to about 12 carbon atoms, more preferably up to about 8 carbon atoms, most preferably up to about 6 carbon atoms), or X may be nitrate ($NO_3$), nitrite ($NO_2$), acetate ($CH_3CO_2$), trifluoroacetate ($CF_3CO_2$), acetylacetonate ($CH_3COCHCOCH_3$), hexafluoroacetylacetonate ($CF_3COCHCOCF_3$), and mixtures thereof. X may be hydrogen. X may be acyls (up to 10 carbons) such as formyl or acetyl. X may be an aliphatic anionic ligand (e.g., containing 2–20 carbon atoms or 2–10 carbon atoms, such as alkenyl (e.g., vinyl, allyl) or alkynyl (e.g, ethynyl)). X may be sulfonates such as methyl sulfonate, trifluoromethanesulfonate, phenylsulfonate, or toluenylsulfonate. X may be cyanide, cyanate, isocyanide, or isocyanate. The X in $RuX_{2-3}$ may be the same or different, for example as in $RuCl_2Br$ or $RuClFBr$.

The arene group of the ruthenium compound (A), e.g., $[RuX_2(arene)]_2$, $RuX_2(arene)(ERR^1R^2)$, $RuX_2(arene)(EH_2R)$, $RuX_2(arene)(EHRR^1)$, and $RuX_2(arene)[E(OR)(OR^1)(OR^2)]$, atoms, preferably up to about 20 carbon atoms, more preferably up to about 15 carbon atoms, substituted or unsubstituted, and mixtures thereof. The substituents of the substituted aromatic ligand may be selected from the group consisting of halogen, alkyl and aryl groups of up to about 25 carbon atoms, preferably up to about 20 carbon atoms, more preferably up to about 12 carbon atoms, and most preferably up to about 8 carbon atoms, trialkylsilyl and triarylsilyl groups of up to about 25 carbon atoms, preferably up to about 20 carbon atoms, more preferably up to about 15 carbon atoms, and most preferably up to about 8 carbon atoms, and mixtures thereof. The aromatic ligand may be selected from alkylbenzenes, polyalkylbenzenes, arylbenzenes, polyarylbenzenes, halobenzenes, haloalkylbenzenes, haloarylbenzenes, alkylnaphthalenes, arylnaphthalenes, polyalkylnaphthalenes, polyarylnaphthalenes, halonaphthalenes, haloalkylnaphthalenes, and haloarylnaphthalenes. The aromatic ligand may be, among others, benzene, toluene, xylene, cumene, cymene, p-cymene, durene, trimethylsilylbenzene, 1,4-bis(trimethylsilyl)benzene, or naphthalene. The arene ligand may be a dicyclic, or a 5–7 atom unicyclic, aromatic compound that contains at least one heteroatom (e.g., nitrogen, sulfur, oxygen, or boron) in the ring, such as pyridine, thiophene, or furan.

The compound B has the formula $ER'_3$ wherein E is phosphorus, arsenic or antimony, and wherein R' is selected from R and (OR) where the R groups are the same or different and are each selected from the group consisting of hydrogen, halogen, alkyl, cycloalkyl, aryl and arylalkyl groups, unsubstituted or substituted, each group of up to about 20 carbon atoms; the substituents may be halogen, or alkyl or aryl moieties of up to 20 carbon atoms. If R' is OR, then R' and R are not hydrogen or halogen. If R' is R, then at least one R is not hydrogen or halogen.

The phosphorus compound (B) preferably is selected from the group consisting of phosphine and phosphite compounds of the formulae $PR_3$, $P(OR)_3$, $PH_2R$, $PHRR^1$, $PRR^1R^2$ and $P(OR)(OR^1)(OR^2)$. R, $R^1$ and $R^2$ are the same or different and are each selected from the group consisting of alkyl, cycloalkyl, aryl and arylalkyl groups, unsubstituted or substituted, each group of up to about 20 carbon atoms (preferably up to about 12 carbon atoms, more preferably up to about 8 carbon atoms, most preferably up to about 6 carbon atoms); the substituents may be halogen (F, Cl, Br, and I), alkyl or aryl moieties of up to 20 carbon atoms (preferably up to about 12 carbon atoms, more preferably up to about 8 carbon atoms, most preferably up to about 6 carbon atoms). The phosphorus compound (B) is preferably a phosphine compound, more preferably a tri-alkyl or -cycloalkyl phosphine typically selected from the group consisting of tricyclohexylphosphine, triisopropylphosphine and tricyclopentylphosphine, or a di-alkyl or -cycloalkyl phosphine, e.g., dicyclohexylphosphine, dicyclohexylphenylphosphine, di-tert-butylphosphine or di-tert-butylchlorophosphine.

The arsenic or antimony compound (B) preferably is selected from the group consisting of arsine or antimony compounds of the formulae $DR_3$, $DH_2R$, $ER_3$, $EH_2R$, $EHRR^1$, and $ERR^1R^2$ wherein E is As (arsenic) or Sb (antimony). R, $R^1$ and $R^2$ are the same or different and are each selected from the group consisting of unsubstituted and substituted alkyl and aryl groups (e.g., groups of up to about 20 or about 12 or about 8 or about 6 carbon atoms). Arsenic compound (B) may be a tri-alkyl, e.g., triisopropylarsine, or a -cycloalkyl arsine, e.g., tricyclohexylarsine or tricyclopentylarsine, or a di-alkyl or -cycloalkyl arsine, e.g., dicyclohexylarsine, di-tert-butylarsine or dicyclohexylphenylarsine. Antimony compound (B) may be a tri-alkyl or -cycloalkyl antimony, e.g. triisopropylantimony, tricyclohexylantimony, or tricyclopentylantimony, or di-alkyl or -cycloalkyl antimony, e.g., dicyclohexylantimony, di-tert-butylantimony or dicyclohexylphenylantimony.

Catalyst compound (C), the compound containing at least one carbon-to-carbon triple bond, can be a substituted or unsubstituted $C_2$ to $C_{20}$ alkyne (preferably up to about 16 carbon atoms, more preferably up to about 12 carbon atoms, most preferably up to about 8 carbon atoms) such as a terminal alkyne, an internal alkyne, or an alkyne possessing one or more (e.g., 1 or 2) aliphatic, alkenyl or aromatic functional substituent groups (preferably up to about 20 carbon atoms, more preferably up to about 12 carbon atoms, most preferably up to about 8 carbon atoms), halogen (F, Cl, Br, and I), ester, hydroxyl, ketone, aldehyde, ether, carboxyl, amide, anhydride, nitrile, silyl or amine functional substituent groups, and mixtures thereof. Catalyst compound (C) can be selected from the group consisting of acetylene ($C_2H_2$), propyne, 1-butyne, 2-butyne, 1-pentyne, 2-pentyne, 1-hexyne, 2-hexyne, 3-hexyne, 1-heptyne, 1-octyne, 1-decyne, 1-dodecyne, trimethylsilylacetylene, phenylacetylene, diphenylacetylene, 2-butyne-1,4-diol, ester derivatives of 2-butyne-1,4-diol such as 1,4-diacetoxy-2-butyne, 2-butyne-1,4-diol monoacetate, 2-butyne-1,4-diol diacetate, 2-butyne-1,4-diol monopropionate, 2-butyne-1,4-diol dipropionate, 2-butyne-1,4-diol monobenzoate, 2-butyne-1,4-diol dibenzoate, propargyl alcohol, propargyl chloride, propargyl bromide, propargyl acetate, propargyl propionate, propargyl butyrate, propargyl benzoate, 1,4-dichloro-2-butyne, 2-butyne-1,4-diol monobutyrate, 2-butyne-1,4-diol dibutyrate, tert-butylacetylene, and di-tert-butylacetylene.

Mole ratios of A:B:C, expressed as compounds, are typically in the range of 1:0.01–100:0.01–500, preferably 1:0.01–100:0.01–100 and more preferably 1.0:0.1–40:0.1–40. Mole ratios of A:B, expressed as compounds, are typically in the range of 1:0.01–100 and preferably 1.0:0.1–40.

It has been found that the presence of hydrogen ($H_2$) improves catalytic activity, reactant conversion, and product yield. The presence of hydrogen (typically at a partial pressure of hydrogen of from about $1 \times 10^{-2}$ mm Hg to about 200 atmospheres, preferably from about 0.1 mm Hg to about 100 atmospheres, more preferably 1 mm Hg to about 20 atmospheres, though generally pressure is not critical) as a catalyst system activator improves the catalyst activity, reactant conversion, and product yield in the process of the invention.

The catalyst system is employed in processes to metathesize olefins, including ring-opening metathesis polymerization of cyclic olefins, metathesis of acyclic olefins, acyclic diene metathesis oligomerization or polymerization, cross-metathesis of cyclic and acyclic olefins, ring-closing metathesis, metathesis depolymerization of unsaturated polymers, and metathesis of functionalized olefins. The catalyst system can successfully metathesize highly-strained cyclic olefins (e.g., norbornene and norbornene derivatives, norbornadiene, cyclobutene and cyclobutene derivatives, and dicyclopentadiene) as well as less-strained cyclic olefins (e.g., cyclopentene, cycloheptene, cyclooctene, or 1,5-cyclooctadiene, cyclodecene, cyclododecene, and 1,5,9-cyclododecatriene). The catalyst system is also employed in metathesis of acyclic olefins. For example, the process may be a metathesis reaction of linear alpha-olefins, a metathesis reaction of linear internal olefins, a metathesis reaction of branched alpha-olefins, a metathesis reaction of branched internal olefins, or a cross-metathesis reaction of combinations of at least two members selected from the groups consisting of linear alpha-olefins, linear internal olefins, branched alpha-olefins, and branched internal olefins. Olefins containing functional groups such as ester, hydroxyl, ketone, aldehyde, ether, carboxyl, amide, anhydride, nitrile, halogen (F, Cl, Br, and I), and/or amine moieties can also be metathesized.

It is preferable that an activator be present as a component of the catalyst system for increased catalytic activity, increased reactant conversion and increased product yield. It has been found that hydrogen, $H_2$, acts as an activator of the catalyst system. It is assumed that the solubility of hydrogen in the liquid phase (with the liquid phase consisting of the reactant olefins either in neat form or dissolved in a solvent) aids in the catalytic activity of the catalyst system. It is well-known that hydrogen is soluble in solvents with greater solubility of hydrogen in liquid media with increased pressure (A. Seidell, *Solubilities of Inorganic and Metal Organic Compounds,* Vol. 1, D. Van Nostrand Co., N.Y., N.Y., 1940, p. 564–567). Such solvents include the solvents listed below.

The catalyst system alternatively can comprise a catalyst component to dehydrogenate a hydrogen-containing compound as an in-situ source of hydrogen under the reaction conditions of the process, such as the dehydrogenation of tetralin to naphthalene and $H_2$, and dehydrogenation of cyclohexyl alcohol to $H_2$ and cyclohexanone in the presence of ruthenium on activated carbon; such dehydrogenation reactions are well known in the art.

As employed in the method of this invention, the catalyst system is dissolved or suspended in a liquid phase, with the liquid phase consisting primarily of the reactant olefins either in neat form or dissolved in a solvent. A variety of solvents may be employed, including aliphatic solvents such as pentane, hexane, heptane, decane, decalin, and dichloromethane, aromatics such as benzene, toluene, xylenes, chlorobenzene, and dichlorobenzene, and others such as diethyl ether and tetrahydrofuran. A solvent is preferred for $RuX_3$ and $RuX_3$ hydrate where X is halogen (F, Cl, Br, I) to dissolve the $RuX_3$ when $RuX_3$ or $RuX_3$ hydrate is used as the ruthenium compound component of the catalyst system. The solvent should be effective at dissolution of the $RuX_3$. Preferred solvents are alcohols, such as methanol, ethanol, propanol, isopropanol, n-butanol, sec-butyl alcohol, t-butyl alcohol, n-hexanol, n-octanol, and benzyl alcohol. Other possible solvents include acetone, ethyl acetate, and water. Combinations of these solvents are also suitable. The use of no solvent is also possible, but not preferred because use of solvent results in greater olefin metathesis reaction rates and yields. Any amount of solvent may be employed, but use of at least the minimum quantity required for dissolution of the $RuX_3$ is preferred and such minimum quantity is easily determined by a person skilled in the art. The volume of solvent may be very small relative to the volume of olefin reactants employed.

The catalyst system can be employed under an atmosphere of nitrogen, argon, helium, air, carbon dioxide, or hydrogen, and typically at a pressure from below atmospheric (i.e., under vacuum) up to about 200 atmospheres. A hydrogen atmosphere is preferred. Generally, a wide range of temperatures, pressures and reaction times can be used. The olefin metathesis process employing the invented catalyst system can typically be at a temperature of from about 0° C. to about 250° C. (preferably about 0° C. to about 200° C., more preferably about 0° C. to about 150° C.), and typically at a pressure of from about $1\times10^{-2}$ mm Hg to about 200 atmospheres (preferably about 0.1 mm Hg to about 100 atmospheres, more preferably about 1 mm Hg to about 20 atmospheres). Typically, the reaction time (or residence time in a continuous reaction) for the olefin metathesis process employing the invented catalyst system can be from about one second to about one day; preferably from about five minutes to about 10 hours. As is well known, side reactions may occur during olefin metathesis reactions. These side reactions include alkylation, isomerization, cyclization and addition across double bonds present in the molecular structure. Surprisingly, it has been found that these side reactions are minimal in cross-metathesis reactions under the conditions of the present invention.

It has been found that linear functional acyclic olefinic compounds comprising monofunctional unsaturated polymers containing functional groups can be prepared in the presence of the catalyst composition of this invention in cross-metathesis reactions with acyclic or cyclic olefinic non-conjugated compounds.

In the presence of reactants comprising cyclic olefinic non-conjugated compounds and polymeric olefinic compounds with functional olefinic compounds, linear difunctional telechelic unsaturated polymers are prepared with at least one internal carbon-to-carbon double bond and terminal groups. These linear non-crosslinked difunctional telechelic unsaturated polymers with reactive terminal groups are suitable for further functionalization or incorporation into other polymers for preparation of block copolymers and other products.

The linear non-crosslinked difunctional telechelic unsaturated polymers prepared by the process of this invention are typically true linear compounds of strictly regular structure with exactly defined terminal groups.

As is well known, side reactions may occur during olefin metathesis reactions. These side reactions include alkylation, isomerization, cyclization and addition across double bonds present in the molecular structure. Surprisingly, it has been found that these side reactions are minimal in cross-metathesis reactions under the conditions of the present invention. The average functionality number of monofunctional polymers prepared by the process of this invention is at least 0.7 (e.g., 0.7 to 1.0) as determined by nuclear magnetic resonance spectroscopy ($^{13}$C NMR which is well known in the art). The average functionality number of telechelic difunctional polymers prepared by the process of this invention is at least 1.7 (e.g., 1.7 to 2.0), as determined by nuclear magnetic resonance spectroscopy ($^{13}$C NMR). The functionality number is determined by the nuclear magnetic resonance spectroscopy procedure described by Nubel, P.O., et al., "Preparation of an ester-terminated telechelic polybutadiene by a two-step olefin metathesis process", *Journal of Molecular Catalysis A: Chemical* (1997), 115: 43–50.

The monofunctional polymers and telechelic difunctional polymers prepared by the process of the instant invention are prepared by metathesis reactions which are cross-metathesis reactions between acyclic olefinic compounds or cross-metathesis reactions between cyclic and acyclic olefinic compounds. Cross-metathesis reactions have been generally classified as being of three categories: (1) exchange of atoms between two olefinic compounds to produce two different olefinic compounds, (2) ring-opening of a cyclic olefinic compound to produce acyclic polymers, and (3) degradation of olefinic polymers to produce oligomers of lower molecular weight. The reactions of the present invention are of the three categories.

Non-crosslinked linear monofunctional and telechelic difunctional polymers obtained by the process of this invention are defined as polymers consisting essentially of strictly linear hydrocarbon chains comprising repeating monomer units of 3 to 30 carbon atoms, said hydrocarbon chains without any side chains or pendant groups which would cause cross-linking. The number of monomer repeating units can be from 3 to about 10,000.

Non-crosslinked linear monofunctional telechelic polymers prepared by the process of this invention are defined as monofunctional polymers having a terminal functional reactive group and an average functionality number which is at least 0.7, as determined by NMR. Non-crosslinked linear difunctional telechelic polymers prepared by the process of this invention are defined as difunctional polymers containing terminal functional end-groups and the average functionality number is at least 1.7, as determined by NMR.

The present invention provides a metathesis catalytic process for preparing non-crosslinked monofunctional and telechelic difunctional polymers from monofunctional olefinic compounds wherein the functionality of a monofunctional polymer is at least 0.7 and the average functionality of a difunctional polymer is at least 1.7, as determined by NMR (nuclear magnetic resonance). The present invention also provides monofunctional and difunctional unsaturated polymers wherein the functional groups are reactive terminal groups and thus are positioned for further functionalization and/or incorporation into other reactive compounds. The present invention also can be used to prepare monofunctional and telechelic difunctional polymers wherein the functional component comprises a terminal functional group, particularly an ester group such as an acetoxy group. Functional groups are defined herein as including ester, hydroxyl, ketone, aldehyde, ether, carboxyl, amide, anhydride, nitrile, halogen (F, Cl, Br, and I), and/or amine moieties.

The following examples are exemplary only and are not to be considered as limiting the scope of the invention:

EXAMPLES 1–43

Example 1

The self-metathesis reaction of 1-octene was performed using ruthenium tribromide hydrate (RuBr$_3$.xH$_2$O) as the ruthenium compound component of the catalyst system:

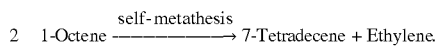

$$2 \; \text{1-Octene} \xrightarrow{\text{self-metathesis}} \text{7-Tetradecene} + \text{Ethylene}.$$

The following stock solutions were prepared:
1. Ruthenium tribromide hydrate (15 mg, Strem Chemicals, 25.9 wt % Ru) was dissolved in 10 mL ethanol (200-proof).
2. Tricyclohexylphosphine (90 mg, 0.32 mmol, "PCy$_3$", Strem Chemicals) was dissolved in 50 mL chlorobenzene under N$_2$ atmosphere.
3. A solution of 2-butyne-1,4-diol diacetate ("BDD", Narchem Corp.) in chlorobenzene was prepared at a concentration of 12.2 mg BDD (0.072 mmol) per mL and stored under N$_2$.

1-Octene (40 mL, 255 mmol, Aldrich), 0.40 mL of the ruthenium tribromide hydrate/ethanol solution (1.5 μmol Ru), 0.62 mL of the PCy$_3$/chlorobenzene solution (4.0 μmol PCy$_3$), 0.53 mL of the BDD/chlorobenzene solution (38 μmol BDD), and 0.40 mL chlorobenzene were added under N$_2$ atmosphere to a 100-mL glass reactor flask equipped with a magnetic stirbar and a water-cooled reflux condenser. The solution was stirred at room temperature under N$_2$. A small aliquot of the liquid was removed via gas-tight syringe for FID GC analysis as a "before reaction" sample. The reactor flask was then immersed in an 80° C. oil bath and a flow of hydrogen gas (H$_2$) was bubbled through the solution in the flask at 1 atm at 50 mL/min flow rate. The flask contents were stirred at 80° C. for 2 hours and the flow of H$_2$ was maintained during this time. After the 2-hour reaction time another small aliquot of the liquid was removed via gas-tight syringe for FID GC analysis ("after reaction" sample). Calculations of 1-octene conversion and tetradecene selectivity were performed using the GC data. The following results were obtained: 1-Octene conversion: 46%; Tetradecene selectivity: 92%.

Example 2

The metathesis reaction of an internal acyclic olefin, methyl oleate (methyl cis-9-octadecenoate), was performed:

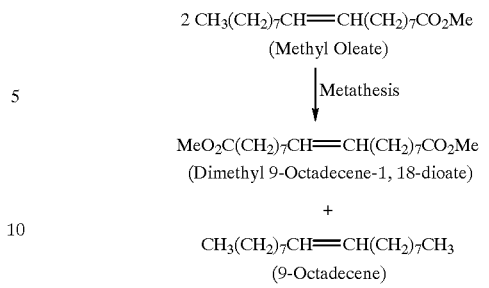

2 CH$_3$(CH$_2$)$_7$CH=CH(CH$_2$)$_7$CO$_2$Me
(Methyl Oleate)

↓ Metathesis

MeO$_2$C(CH$_2$)$_7$CH=CH(CH$_2$)$_7$CO$_2$Me
(Dimethyl 9-Octadecene-1, 18-dioate)

+

CH$_3$(CH$_2$)$_7$CH=CH(CH$_2$)$_7$CH$_3$
(9-Octadecene)

To a glass reaction flask were added 20 mL methyl oleate (60 mmol, Aldrich 99%), 0.15 mL of a 0.08 M ruthenium trichloride hydrate/ethanol solution (12 μmol Ru), 0.82 mL of a 0.036 M PCy$_3$/chlorobenzene solution (0.030 mmol PCy$_3$), and 0.94 mL of a 0.30 M BDD/chlorobenzene solution (0.28 mmol BDD). The reaction flask was then immersed in an 90° C. oil bath and a flow of hydrogen gas (H$_2$) was bubbled through the solution in the flask at 1 atm at 50 mL/min flow rate. The flask contents were stirred at 90° C. for 4 hours and the flow of H$_2$ was maintained during this time. After the 4-hour reaction time a small aliquot of the liquid was removed via gas-tight syringe for FID GC analysis. GC analysis indicated that the metathesis reaction had proceeded cleanly, yielding 9-octadecene and dimethyl octadecene-1, 18-dioate products. Conversion of methyl oleate to these products was determined to be approximately 13%. The only other significant product detected in the GC analysis was an apparent isomer of methyl oleate, produced in approximately 1% yield.

Examples 3–6

Self-metathesis reactions of 1-tetradecene (1-C$_{14}$$^=$), yielding internal C$_{26}$ olefin product, were performed using a catalyst system comprised of ruthenium trichloride and one of four different phosphorus compounds (phosphines).

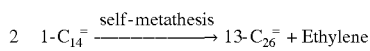

$$2 \; \text{1-C}_{14}^= \xrightarrow{\text{self-metathesis}} \text{13-C}_{26}^= + \text{Ethylene}$$

To a 100 mL glass reaction flask equipped with a water-cooled reflux condenser were added 40 mL (31 g) 1-tetradecene (~80% pure), 0.095 mL of a 0.041 M ruthenium trichloride hydrate/1-hexanol solution (3.9 μmol Ru), phosphine, 0.32 mL of a 0.30 M BDD/chlorobenzene solution (0.096 mmol BDD), and a 1.0 mL undecane (as an internal standard for GC calculations of conversions) under N$_2$ atmosphere. The solution was magnetically stirred at room temperature under N$_2$. A small aliquot of the liquid was removed via gas-tight syringe for FID GC analysis as a "before reaction" sample. The reactor flask was then immersed in a 90° C. oil bath and a flow of hydrogen gas (H$_2$) was bubbled through the solution in the flask at 1 atm at 50 mL/min flow rate. The flask contents were stirred at 90° C. for 2 hours and the flow of H$_2$ was maintained during this time. After the 2-hour reaction time another small aliquot of the liquid was removed via gas-tight syringe for FID GC analysis. GC analyses indicated the metathesis reaction product, C$_{26}$ olefin, was the predominant non-gaseous reaction product. (No analyses of gaseous products, such as ethylene, were performed). Calculations of 1-tetradecene conversions were performed using the GC data (using undecane as internal standard); the following results were obtained:

TABLE 1

| Example | Phosphine Employed | Amount of Phosphine Employed (μmole) | 1-Tetradecene Conversion (after 2 hrs at 90° C.) |
|---|---|---|---|
| 3 | PCy$_3$ (Tricyclohexylphosphine) | 9.9 | 58% |
| 4 | P(i-Pr)$_3$ (Triisopropylphosphine) | 8.0 | 14% |
| 5 | PCl(t-Bu)$_2$ (Di-tert-butylchlorophosphine) | 9.9 | 33% |
| 6 | PH(t-Bu)$_2$ (Di-tert-butylphosphine) | 9.9 | 35% |

Examples 7–9

The self-metathesis reaction of the linear alpha-olefin 1-octene was performed using a ruthenium-containing catalyst system:

$$2 \text{ 1-Octene} \xrightarrow{\text{self-metathesis}} \text{7-Tetradecene} + \text{Ethylene}$$

A stock solution of [RuCl$_2$(p-cymene)]$_2$ (80 mg, 0.13 mmol) and tricyclohexylphosphine (90 mg, 0.32 mmol) in 100 mL chlorobenzene was prepared under N$_2$ atmosphere. A 2.5-mL portion of this stock solution was added under N$_2$ at room temperature to a 100 mL round-bottom reactor flask equipped with a magnetic stirbar and a water-cooled reflux condenser. 1-Octene (40 mL, 255 mmol) and 0.3 mL of a heptane solution of alkyne containing 19–20 μmol of alkyne were also added to the reactor flask. The contents of the reactor flask was stirred at room temperature and a small aliquot of the liquid was removed via gas-tight syringe for FID GC (flame ionization detector gas chromatography) analysis as a "before reaction" sample. The reactor flask was then immersed in a 60° C. oil bath and the flask contents were stirred at 60° C. for 4 hours under N$_2$ at atmospheric pressure. Evolved gases were allowed to escape from the flask through an oil bubbler outlet connected to the reflux condenser. After the 4-hour reaction time another small aliquot of the liquid was removed via gas-tight syringe for FID GC analysis ("after reaction" sample). Calculations of 1-octene conversion and tetradecene selectivity were performed using the GC data. Tetradecene selectivity is defined as 100%(observed wt % tetradecene selectivity)/(87.5%), where 87.5% is the theoretical maximum wt % tetradecene selectivity based upon reaction stoichiometry. Results are given in the following table:

TABLE 2

| Example | Alkyne Employed | 1-Octene Conversion | Tetradecene Selectivity |
|---|---|---|---|
| 7 | 2-Butyne-1,4-diol diacetate | 29% | 86% |
| 8 | Propargyl Acetate | 18% | 80% |
| 9 | 1-Decyne | 6% | 68% |

Examples 10–12

These examples were performed by the same procedure as Examples 7–9 except that immediately after the reactor flask was immersed in the 60° C. oil bath a flow of hydrogen gas (H$_2$) was bubbled through the solution in the flask at 1 atm for 15 minutes at 100 mL/min flow rate. The hydrogen gas passed into the solution from the immersed tip of a stainless steel syringe needle, and exited the flask through an oil bubbler outlet connected to the reflux condenser. After 15 minutes the flow of hydrogen into the flask was ceased and the flask contents were stirred at 60° C. for 3.75 hours (with evolved gases allowed to escape), then a liquid aliquot was removed for GC analysis. Results are given in the following table:

TABLE 3

| Example | Alkyne Employed | 1-Octene Conversion | Tetradecene Selectivity |
|---|---|---|---|
| 10 | 2-Butyne-1,4-diol diacetate | 34% | 89% |
| 11 | Propargyl Acetate | 33% | 87% |
| 12 | 1-Decyne | 29% | 89% |

Examples 13–14

Examples 13–14 illustrate olefin metathesis of a linear alpha-olefin (1-octene) using a ruthenium-containing catalyst containing an arsenic or antimony compound as compound (B) instead of a phosphorus compound:

Example 13

The self-metathesis reaction of the linear alpha-olefin 1-octene is performed using a ruthenium-containing catalyst system:

$$2 \text{ 1-Octene} \xrightarrow{\text{self-metathesis}} \text{7-Tetradecene} + \text{Ethylene}$$

A stock solution of [RuCl$_2$(p-cymene)]$_2$ (80 mg, 0.13 mmol) and tricyclohexylarsine (As(cyclohexyl)$_3$, 100 mg, 0.3 mmol) in 100 mL chlorobenzene is prepared under N$_2$ atmosphere. A 2.5-mL portion of this stock solution is added under N$_2$ at room temperature to a 100 mL round-bottom reactor flask equipped with a magnetic stirbar and a water-cooled reflux condenser. 1-Octene (40 mL, 255 mmol) and 0.3 mL of a heptane solution containing 20 μmol of 2-butyne-1,4-diol diacetate are also added to the reactor flask. The contents of the reactor flask is stirred at room temperature and a small aliquot of the liquid is removed via gas-tight syringe for FID GC (flame ionization detector gas chromatography) analysis as a "before reaction" sample. The reaction flask is then immersed in a 60° C. oil bath and a flow of hydrogen gas (H$_2$) is bubbled through the solution in the flask at 1 atm for 15 minutes at 100 mL/min flow rate. The hydrogen gas is passed into the solution from the immersed tip of a stainless steel syringe needle, and exits the flask through an oil bubbler outlet connected to the reflux condenser. After 15 minutes the flow of hydrogen into the flask is ceased and the flask contents are stirred at 60° C. Gases evolving during the reaction are allowed to escape from the flask through the oil bubbler outlet. After four hours at 60° C. a small aliquot of liquid is removed for GC analysis. GC analysis indicates conversion of 1-octene to tetradecene, the expected product of the self-metathesis reaction.

Example 14

The self-metathesis reaction of the linear alpha-olefin 1-octene is performed using the ruthenium-containing catalyst system. A stock solution of [RuCl$_2$(p-cymene)]$_2$ (80 mg, 0.13 mmol) and tricyclohexylantimony (Sb(cyclohexyl)$_3$, 110 mg, 0.3 mmol) in 100 mL chlorobenzene is prepared under N$_2$ atmosphere. A 2.5-mL portion of this stock solution is added under N$_2$ at room temperature to a 100 mL round-bottom reactor flask equipped with a magnetic stirbar and a water-cooled reflux condenser. 1-Octene (40 mL, 255 mmol) and 0.3 mL of a heptane solution containing 20 μmol of 2-butyne-1,4-diol diacetate are also added to the reactor flask. The contents of the reactor flask are stirred at room temperature and a small aliquot of the liquid is removed via gas-tight syringe for FID GC (flame ionization detector gas chromatography) analysis as a "before reaction" sample. The reactor flask is then immersed in a 60° C. oil bath and a flow of hydrogen gas (H$_2$) is bubbled through the solution in the flask at 1 atm for 15 minutes at 100 mL/min flow rate. The hydrogen gas is passed into the solution from the immersed tip of a stainless steel syringe needle, and exits the flask through an oil bubbler outlet connected to the reflux condenser. After 15 minutes the flow of hydrogen into the flask is ceased and the flask contents are stirred at 60° C. Gases evolving during the reaction are allowed to escape from the flask through the oil bubbler outlet. After four hours at 60° C. a small aliquot of liquid is removed for GC analysis. GC analysis indicates conversion of 1-octene to tetradecene, the expected product of the self-metathesis reaction.

Example 15

The metathesis reaction of the acyclic linear internal olefin 2-octene is performed using a ruthenium-containing catalyst system:

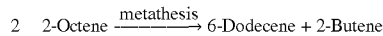

A stock solution of [RuCl$_2$(p-cymene)]$_2$ (80 mg, 0.13 mmol) and tricyclohexylphosphine (90 mg, 0.32 mmol) in 100 mL chlorobenzene is prepared under N$_2$ atmosphere. A 2.5-mL portion of this stock solution is added under N$_2$ at room temperature to a 100 mL glass round-bottom reactor flask equipped with a magnetic stirbar and a water-cooled reflux condenser. 2-Octene (30 g, 270 mmol) and 0.3 mL of a heptane solution containing 20 μmol of 2-butyne-1,4-diol diacetate are also added to the reactor flask. The contents of the reactor flask is stirred at room temperature and a small aliquot of the liquid is removed via gas-tight syringe for FID GC (flame ionization detector gas chromatography) analysis as a "before reaction" sample. The reactor flask is then immersed in a 60° C. oil bath and a flow of hydrogen gas (H$_2$) is bubbled through the solution in the flask at 1 atm for 15 minutes at 100 mL/min flow rate. The hydrogen gas is passed into the solution from the immersed tip of a stainless steel syringe needle, and exits the flask through an oil bubbler outlet connected to the reflux condenser. After 15 minutes the flow of hydrogen into the flask is ceased and the flask contents are stirred at 60° C. After four hours at 60° C. a small aliquot of liquid is removed for GC analysis. GC analysis indicates conversion of 2-octene to dodecene and 2-butene, the expected products of the metathesis reaction.

It is expected that the catalyst of the present invention will successfully effect the metathesis of branched acyclic olefins since it can do so with linear olefins. Also, it is expected that cross-metathesis reactions will proceed since the reverse reactions of 1-octene self-metathesis and 2-octene self-metathesis are cross-metathesis reactions, and since metathesis reactions are reversible it follows that the demonstration that the catalyst can effect the forward (self-metathesis) reaction indicates that the catalyst will also be able to effect the reverse (cross-metathesis) reaction.

Example 16

The self-metathesis reaction of the linear alpha-olefin 1-octene was performed using the ruthenium-based catalyst system. A stock solution of RuCl$_2$[P(C$_6$H$_5$)$_3$]$_3$ (40 mg, 0.042 mmol) and tricyclohexylphosphine (14 mg, 0.050 mmol) in 100 mL chlorobenzene was prepared under N$_2$ atmosphere. A 3.8-mL portion of this stock solution was added under N$_2$ at room temperature to a 100 mL glass round-bottom reactor flask equipped with a magnetic stirbar and a water-cooled reflux condenser. 1-Octene (40 mL, 255 mmol) and 0.63 mL of a chlorobenzene solution of 2-butyne-1,4-diol diacetate containing 38 μmol of 2-butyne-1,4-diol diacetate were also added to the reactor flask. The contents of the reactor flask was stirred at room temperature and a small aliquot of the liquid was removed via gas-tight syringe for FID GC (flame ionization detector gas chromatography) analysis as a "before reaction" sample. The reactor flask was then immersed in an 80° C. oil bath and a flow of hydrogen gas (H$_2$) was bubbled through the solution in the flask at 1 atm for 30 minutes at 50 mL/min flow rate. The hydrogen gas passed into the solution from the immersed tip of a stainless steel syringe needle, and exited the flask through an oil bubbler outlet connected to the reflux condenser. A small aliquot of the liquid was then removed via gas-tight syringe for FID GC analysis ("after reaction" sample). From the GC data 1-octene conversion was determined to be 7% and tetradecene selectivity was 91%. (Tetradecene selectivity is defined as 100%(observed wt % tetradecene selectivity)/(87.5%), where 87.5% is the theoretical maximum wt % tetradecene selectivity based upon reaction stoichiometry.)

Example 17

The self-metathesis reaction of the linear alpha-olefin 1-octene was performed using ruthenium trichloride hydrate RuCl$_3$.xH$_2$O as the ruthenium compound component of a ruthenium-containing catalyst system:

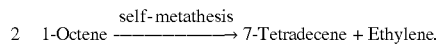

The following stock solutions were prepared:
1. Ruthenium trichloride hydrate (80 mg, Strem Chemicals, 40.1 wt % Ru) was dissolved in 10 mL ethanol (200-proof). RuCl$_3$.xH$_2$O was used in solution form; it was dissolved in alcohol.
2. Tricyclohexylphosphine (93 mg, 0.33 mmol, "PCy$_3$", Strem Chemicals) was dissolved in 50 mL heptane under N$_2$ atmosphere.
3. A solution of 2-butyne-1,4-diol diacetate ("BDD", Narchem Corp.) in chlorobenzene was prepared at a concentration of 11.5 mg BDD (0.068 mmol) per mL and stored under N$_2$.

The 1-octene metathesis reaction was performed in a glass 100 mL round-bottom reactor flask equipped with a magnetic stirbar and a water-cooled reflux condenser. 1-Octene (40 mL, 255 mmol, Aldrich), 100 μL of the ruthenium trichloride hydrate/ethanol solution (3.2 μmol Ru), 1.20 mL of the PCy$_3$/heptane solution (8.0 μmol PCy$_3$), 1.14 mL of the BDD/chlorobenzene solution (77 μmol BDD), and 0.40 mL chlorobenzene were added to the reactor flask and stirred at room temperature under N$_2$. A small aliquot of the liquid was removed via gas-tight syringe for FID GC (flame ionization detector gas chromatography) analysis as a "before reaction" sample. The reactor flask was then immersed in an 80° C. oil bath and a flow of hydrogen gas (H$_2$) was bubbled through the solution in the flask at 1 atm at 50 mL/min flow rate. (The hydrogen gas passed into the solution from the immersed tip of a stainless steel syringe needle, and exited the flask through an oil bubbler outlet connected to the reflux condenser). The flask contents were stirred at 80° C. for 2 hours and the flow of H$_2$ was maintained during this time. After the 2-hour reaction time another small aliquot of the liquid was removed via gas-tight syringe for FID GC analysis ("after reaction" sample). Calculations of 1-octene conversion and tetradecene selectivity were performed using the GC data. The following results were obtained: 1-Octene conversion: 36%; Tetradecene selectivity: 86% (tetradecene selectivity is defined here as 100% (observed wt % tetradecene selectivity)/ (87.5%), where 87.5% is the theoretical maximum wt % tetradecene selectivity based upon reaction stoichiometry).

Example 18

This example was performed analogously to Example 17, except that the ruthenium trichloride hydrate was dissolved in 1-butanol (Aldrich).

The following stock solutions were prepared:
1. Ruthenium trichloride hydrate (80 mg, Strem Chemicals, 40.1 wt % Ru) was dissolved in 10 mL 1-butanol.
2. Tricyclohexylphosphine (93 mg, 0.33 mmol, "PCy$_3$", Strem Chemicals) was dissolved in 50 mL heptane under N$_2$ atmosphere.
3. A solution of 2-butyne-1,4-diol diacetate ("BDD", Narchem Corp.) in chlorobenzene was prepared at a concentration of 12.1 mg BDD (0.071 mmol) per mL and stored under N$_2$.

1-Octene (40 mL, 255 mmol, Aldrich), 100 μL of the ruthenium trichloride hydrate/1-butanol solution (3.2 μmol Ru), 1.20 mL of the PCy$_3$/heptane solution (8.0 μmol PCy$_3$), 1.08 mL of the BDD/chlorobenzene solution (77 μmol BDD), and 0.40 mL chlorobenzene were added to the reactor flask and stirred at room temperature under N$_2$. A small aliquot of the liquid was removed via gas-tight syringe for FID GC (flame ionization detector gas chromatography) analysis as a "before reaction" sample. The reactor flask was then immersed in an 80° C. oil bath and a flow of hydrogen gas (H$_2$) was bubbled through the solution in the flask at 1 atm at 50 mL/min flow rate. (The hydrogen gas passed into the solution from the immersed tip of a stainless steel syringe needle, and exited the flask through an oil bubbler outlet connected to the reflux condenser). The flask contents were stirred at 80° C. for 2.5 hours and the flow of H$_2$ was maintained during this time. After the 2.5-hour reaction time another small aliquot of the liquid was removed via gas-tight syringe for FID GC analysis ("after reaction" sample). Calculations of 1-octene conversion and tetradecene selectivity were performed using the GC data. The following results were obtained: 1-Octene conversion: 38%; Tetradecene selectivity: 89%.

Example 19

This example illustrates the effect of the presence of a compound containing a carbon-to-carbon triple bond wherein the mole ratio of ruthenium compound (A) to phosphorus compound (B) and carbon-to-carbon triple bond (C) is 1.0:4.0:0.22. Conversion of 1,5-cyclooctadiene (1,5-COD), in the presence of 1,4-diacetoxy-2-butene, 1,4-DAB, to acetate-terminated 1,4-polybutadiene in an inert atmosphere of nitrogen after a reaction time of 3 hours at 90° C. was 35 wt. % with a corresponding conversion of 1,4-DAB to 17 wt. %. After 22 hours at 90° C., conversion to acetate-terminated 1,4-polybutadiene of the 1,4-COD was 39 wt. % and 1,4-DAB was 27 wt. %.

A solution consisting of 0.098 g [(RuCl$_2$(p-cymene)]$_2$ (0.16 mmol, Strem Chemicals, Inc.,) 0.18 g tricyclohexylphosphine (0.64 mmol, Aldrich), 3.7 mL cis-1,4-diacetoxy-2-butene ("cis-1,4-DAB", 23 mmol, 95+% purity, TCI America, lot number FCZ02), 15.0 mL cis,cis-1,5-cyclooctadiene ("1,5-COD", 122 mmol, 99.9% purity by GC analysis), and 35 mL chlorobenzene (Aldrich HPLC grade, dried over 4A molecular sieves) was charged into a 100-mL glass round-bottom flask under N$_2$ at atmospheric pressure (15 psia). Flame ionization detector (FID) gas chromatographic (GC) analysis of the cis-1,4-DAB indicated that it contained 0.15 wt. % of the alkyne 1,4-diacetoxy-2-butyne; thus, the above solution contained 0.035 mmol 1,4-diacetoxy-2-butyne (thus the commercial cis-1,4-DAB product contained 1,4-diacetoxy-2-butyne). The flask containing the solution was immersed in a 90° C. oil bath and the solution was magnetically stirred under nitrogen atmosphere. After 3 hours at 90° C. FID GC analysis of the solution indicated that COD conversion was 35 wt. % and DAB conversion was 17 wt. %. After 22 hours (at 90° C.) GC analysis indicated that COD conversion was 39 wt. % and DAB conversion was 27 wt. %. The reaction solution was then cooled to room temperature. Chlorobenzene solvent, COD, and some of the remaining DAB were removed by rotary evaporation under vacuum (1.5 hours at 80–95° C., 0.2–0.4 mm Hg), affording 5.2 grams of a brown, low-viscosity oily liquid product. This product contained some remaining DAB (6 wt. % as indicated by $^{13}$C NMR analysis). GPC analysis of the product was as follows: $M_n$=370, $M_w$=2590, $M_w/M_n$=7 (tetrahydrofuran (THF) solvent; polybutadiene calibration; calculation of molecular weights included remaining DAB).

A sample of the product was dissolved in CDCl$_3$ and analyzed by $^{13}$C and $^1$H NMR spectroscopy using a Varian VXR-300 spectrometer. (Chromium acetylacetonate was added to the solution as a relaxation agent for $^{13}$C NMR studies). NMR analyses indicated that the product possessed a 1,4-polybutadiene backbone structure with a 72:28 cis/ trans carbon-carbon double bond ratio. The proportion of chain end groups observed by $^{13}$C NMR was 97 mole % acetate-type endgroups (—CH$_2$OC(O)CH$_3$) and 3 mole % vinyl endgroups (—CH═CH$_2$).

The analyses indicate that the product was a low molecular weight polybutadiene material with acetate-type functional groups as the predominant type of chain end group. This is the expected product of the cross-metathesis reaction of 1,5-COD with 1,4-DAB. Details are in Table 4.

Example 20

This example was performed according to the procedure of Example 19 except that the reaction was performed under an atmosphere of hydrogen ($H_2$) at atmospheric pressure (15 psia) and demonstrates the beneficial effect of hydrogen upon catalytic activity, reactant conversion, and product yield. The presence of hydrogen, $H_2$, caused the conversion of 1,5-cyclooctadiene in the presence of 1,4-diacetoxy-2-butene to acetate-terminated 1,4-polybutadiene to increase from 35 wt. %, as in Example 19, to 70 wt. %. A corresponding increase in conversion of 1,4-diacetoxy-2-butene from 19 wt. %, Example 19, to 34 wt. % also occurred.

A separate solution consisting of 0.098 g [$RuCl_2$(p-cymene)]$_2$ (0.16 mmol, Strem Chemicals, Inc.), 0.18 g tricyclohexylphosphine (0.64 mmol, Aldrich), 3.7 mL cis-1,4-diacetoxy-2-butene ("cis-1,4-DAB", 23 mmol, 95+% purity, TCI America, lot number FCZ02), 15.0 mL cis,cis-1,5-cyclooctadiene ("1,5-COD", 122 mmol, 99.9% purity by GC analysis), and 35 mL chlorobenzene (Aldrich HPLC grade, dried over 4A molecular sieves) was charged into a 100-mL glass round-bottom flask under $N_2$ atmosphere. FID GC analysis of the cis-1,4-DAB indicated that it contained 0.15 wt. % of the alkyne 1,4-diacetoxy-2-butyne; thus, the solution contained 0.035 mmol 1,4-diacetoxy-2-butyne. The flask was immersed in a 90° C. oil bath. Hydrogen gas ($H_2$) was then bubbled through the solution in the flask at atmospheric pressure (15 psia) for 10 minutes at 100 mL/min flow rate. (The hydrogen gas passed into the solution from the immersed tip of a stainless steel syringe needle, and exited the flask through tubing connected from the headspace of the flask to an oil bubbler). After the 10 minutes, the flow of the hydrogen into the flask was ceased. The solution was then stirred magnetically at 90° C. under the static hydrogen atmosphere (15 psia). After 3 hours (at 90° C.) GC analysis of the solution indicated that COD conversion was 70 wt. % and DAB conversion was 34 wt. %. After 22 hours (at 90° C.) GC analysis indicated that COD conversion was 76 wt. % and DAB conversion was 44 wt. %. It is to be noted that these conversions are approximately twice as high as those that were obtained in Example 19. The only change from Example 19 was the presence of hydrogen.

The reaction solution was then cooled to room temperature. Chlorobenzene solvent, COD, and some of the remaining DAB were removed by rotary evaporation under vacuum (1 hour at 80° C., 0.2 mm Hg), affording 10.75 grams of a brown, low-viscosity oily liquid product. It is to be noted that this yield of crude product is about twice that obtained in Example 19. This crude product contained some remaining DAB (4 wt. % as indicated by $^{13}C$ NMR analysis). GPC analysis of the crude product was as follows: $M_n$=410, $M_w$=2200, $M_w/M_n$=5.4 (THF solvent; polybutadiene calibration; calculation of molecular weights included remaining DAB). A sample of the crude product was dissolved in chloroform-d ($CDCl_3$) and analyzed by $^{13}C$ and $^1H$ NMR spectroscopy using a Varian VXR-300 spectrometer. (Chromium acetylacetonate was added to the solution as a relaxation agent for $^{13}C$ NMR studies). NMR analyses indicated that the product possessed a 1,4-polybutadiene backbone structure with a 69:31 cis/trans carbon-carbon double bond ratio. The proportion of chain end groups observed by $^{13}C$ NMR was 98 mole % acetate-type endgroups (—$CH_2OC(O)CH_3$) and 2 mole % vinyl endgroups (—CH=$CH_2$).

The analyses indicate that this product was a low molecular weight polybutadiene material with acetate-type functional groups as the predominant type of chain end group. This is the expected product of the cross-metathesis reaction of 1,5-COD with 1,4-DAB.

This product was further treated to remove catalyst residues and DAB as follows. The product (~8.4 grams) was dissolved in chlorobenzene (25 mL) containing 50 mg butylated hydroxytoluene (BHT). This solution was filtered through a 1-inch diameter column containing 20 grams of 200-mesh silica gel (Aldrich). Afterward the column was washed with chlorobenzene (5×50 mL) and the washings were added to the filtrate. Removal of solvent by rotary evaporation under vacuum afforded 5.6 grams of a light brown oil. The oil was washed twice with 70-mL portions of methanol; the washes were performed by vigorously stirring the methanol/oil mixture at room temperature, allowing the mixture to stand for phases to separate, and then removing and discarding the methanol phase. Residual methanol was removed from the washed oil by rotary evaporation under vacuum (1 hour at 80° C., 0.4 mm Hg), affording 4.8 grams of a light brown, low-viscosity oily liquid product (labeled 19303-155). GPC analysis of this treated product was as follows: $M_n$=840, $M_w$=2490, $M_w/M_n$=3.0 (THF solvent; polybutadiene calibration). NMR analyses (as described above) indicated that the treated product contained less than 0.5 wt. % DAB. NMR analyses also indicated that the treated product possessed a 1,4-polybutadiene backbone structure with a 69:31 cis/trans carbon-carbon double bond ratio and that the proportion of chain end groups was 98 mole % acetate-type endgroups and 2 mole % vinyl endgroups. Ruthenium content was measured at 0.047 wt. % by XRF analysis. Details are in Table 4.

Example 21

This example illustrates the effect of changing the mole ratio of catalyst components, A:B:C, to 1.0:2.0:0.44, as compared with catalyst component ratio of Examples 19 and 20. Reaction temperature was decreased to 60° C. from 90° C. Reaction time increased to 4 hours from 3 hours. Reaction pressure was increased from atmospheric pressure (15 psia), as in Examples 19 and 20, to 17 psig under $H_2$ gas. Conversion of 1,4-COD increased to 57 wt. % as compared with 1,4-COD conversion of Example 19, 35 wt. %, but decreased from 70 wt. % of Example 20.

A solution consisting of 0.098 g [$RuCl_2$(p-cymene)]$_2$ (0.16 mmol), 0.090 g tricyclohexylphosphine (0.32 mmol), 7.4 mL cis-1,4-DAB (47 mmol), 30.0 mL 1,5-COD (244 mmol), and 10 mL chlorobenzene was charged into a 6-oz glass Fisher-Porter bottle under $N_2$ atmosphere (15 psia). Due to the presence of 0.15 wt. % 1,4-diacetoxy-2-butyne in the cis-1,4-DAB, the solution contained 0.07 mmol 1,4-diacetoxy-2-butyne. The bottle was sealed and then immersed in a 60° C.-oil bath and the solution was magnetically stirred for 20 minutes to dissolve all the solids. The bottle was then pressurized to 17 psig with hydrogen gas ($H_2$). After pressurization, the bottle was sealed off under static hydrogen pressure (valve to hydrogen source was closed) and the solution was stirred for 4 hours (since hydrogen pressurization) at 60° C. At the end of the 4 hours, the pressure in the bottle had decreased to 6 psig. The bottle was cooled to room temperature and depressurized, and the solution was analyzed by FID GC to determine reactant conversions. Calculated COD conversion was 57 wt. %; DAB conversion was 27 wt. %.

The reaction solution was decolorized by adding 5 grams charcoal (100-mesh Darco G-60 brand) and 50 mg BHT, stirring the solution at room temperature under $N_2$ for about ½ hour, and filtering off the charcoal. Chlorobenzene solvent, COD, and most of the remaining DAB were removed by rotary evaporation under vacuum (1 hour at 90° C., 0.1–1 mm Hg), affording 12.6 grams of a yellow, oily liquid crude product. The crude product was then washed three successive times with 150 mL portions of methanol;

the washes were performed by vigorously stirring the methanol/oil mixture at room temperature, allowing the mixture to stand for phases to separate, and then removing and discarding the methanol phase. Residual methanol was removed from the washed oil by rotary evaporation under vacuum (90° C., 0.1–1 mm Hg), affording 9.5 grams of a yellow, oily liquid final product.

GPC analysis of the final product was as follows: $M_n=1400$, $M_w=2620$, $M_w/M_n=1.9$ (THF solvent; polybutadiene calibration). NMR analyses (as described above, except using a Varian Unity-500 spectrometer) indicated that the final product possessed a 1,4-polybutadiene backbone structure with a 69:31 cis/trans carbon-carbon double bond ratio and that end groups was 99+ mole % acetate-type endgroups and less than 1 mole % vinyl endgroups. Also, the NMR analyses indicated that about 1% or less of the carbon-carbon double bonds in the polybutadiene backbone were hydrogenated (relative to a pure unsaturated 1,4-polybutadiene backbone structure). Ruthenium content was measured at 174 ppm by XRF analysis. Details are in Table 4.

Example 22

This example illustrates the effect of increasing the mole ratio of the carbon-to-carbon triple bond (C) in catalyst components A:B:C, to 1.0:2.0:3.0, an increase in component (C) of approximately 7-fold. All other reaction conditions were as in Example 21. Conversion of 1,4-COD increased to 86 wt. % from 57 wt. % of Example 21.

This example was performed according to the procedure of Example 21 except that additional 1,4-diacetoxy-2-butyne was added to the reaction solution. To do this, a stock solution of 1,4-diacetoxy-2-butyne (0.82 g, Aldrich) in chlorobenzene (10 mL total solution volume) was prepared. A 1.0 mL portion of this stock solution, corresponding to 0.48 mmol (0.082 g), 1,4-diacetoxy-2-butyne, was added to a reaction solution consisting of 0.098 g [RuCl$_2$(p-cymene)]$_2$ (0.16 mmol), 0.090 g tricyclohexylphosphine (0.32 mmol), 7.4 mL cis-1,4-DAB (47 mmol), 30.0 mL 1,5-COD (244 mmol), and 10 mL chlorobenzene solvent in a 6-oz. glass Fisher-Porter bottle under N$_2$ atmosphere (15 psia). The reaction was performed at 60° C. with an initial hydrogen pressure of 17–18 psig. After 4 hours reaction time the bottle pressure had decreased to 13 psig. GC analyses after 4 hours reaction time indicated 86% COD conversion and 46% DAB conversion, substantially greater than the conversions obtained in Example 21 (which did not have additional 1,4-diacetoxy-2-butyne added to the reaction solution). Also, GC analyses indicated essentially complete conversion of the 1,4-diacetoxy-2-butyne after 4 hours reaction time.

The reaction product was decolorized, washed, and isolated by the procedure described in Example 21. Crude product was obtained in 20.4 gram yield; 15.7 grams of the final product, a light-brown oily liquid, was obtained. Both yields are substantially greater than those obtained in Example 21. GPC analysis of the final product was as follows: $M_n=1150$, $M_w=2140$, $M_w/M_n=1.9$ (THF solvent; polybutadiene calibration). NMR analyses (as described in Example 21) indicated that the final product possessed a 1,4-polybutadiene backbone structure with a 63:37 cis/trans carbon-carbon double bond ratio and that the proportion of chain end groups was 99.5+ mole % acetate-type endgroups and less than 0.5 mole % vinyl endgroups. Also, the NMR analyses indicated that less than 1% of the carbon-carbon double bonds in the polybutadiene backbone were hydrogenated (relative to a pure unsaturated 1,4-polybutadiene backbone structure). Ruthenium content was measured at 86 ppm by XRF analysis. Details are in Table 4.

The acetate-terminated polybutadiene products of Examples 21 and 22 can be converted to hydroxyl-terminated polybutadiene products by thermal or catalyzed hydrolysis or alcoholysis reactions, such as base- or acid-catalyzed hydrolysis:

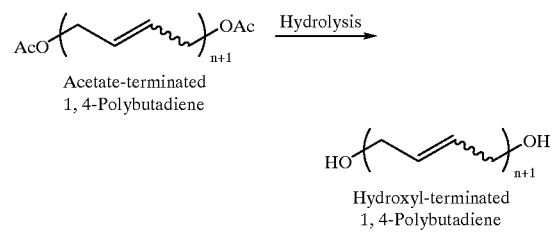

Acetate-terminated 1,4-Polybutadiene

Hydroxyl-terminated 1,4-Polybutadiene

Example 23

This example demonstrates the beneficial effect that the hydrogen catalyst activator has with respect to increasing reaction rate and reactant conversions in the olefin metathesis reaction.

This example was performed according to the procedure of Example 22 except that the reaction was performed without the presence of hydrogen; the reaction of this example was performed under N$_2$ atmosphere (15 psia). (The only other difference was that 9 mL chlorobenzene solvent was employed instead of 10 mL as in Example 22). After 4 hours reaction time (at 60° C.), GC analyses indicated only 5% COD conversion and no detectable DAB conversion. Details are in Table 4.

Examples 24–27

Examples 24–27 demonstrate the ability of this catalyst system to effect the ring-opening metathesis polymerization (ROMP) of a low-strain cyclic olefin, cis,cis-1,5-cyclooctadiene ("1,5-COD"), to yield 1,4-polybutadiene:

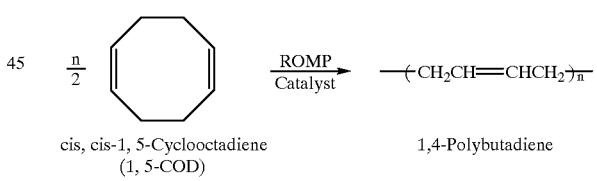

cis, cis-1, 5-Cyclooctadiene (1, 5-COD)

1,4-Polybutadiene

Example 24

This example illustrates ring-opening metathesis polymerization of a cyclic olefin to prepare a high molecular weight polymer in the presence of a catalyst comprising a ruthenium compound (A), a phosphorus compound (B), and a carbon-to-carbon triple bond (C), wherein the mole ratio of A:B:C is 1.0:2.0:3.0.

The alkyne employed was a non-terminal alkyne, 3-hexyne. A stock solution of 3-hexyne (Aldrich) in chlorobenzene was prepared with a concentration of 0.039 g 3-hexyne/mL. A reaction solution consisting of 0.098 g [RuCl$_2$(p-cymene)]$_2$ (0.16 mmol), 0.090 g tricyclohexylphosphine (0.32 mmol), 1.0 mL of the 3-hexyne stock solution (0.48 mmol 3-hexyne), 30.0 mL 1,5-COD (244 mmol), and 9 mL chlorobenzene solvent was charged into a 6-oz. glass Fisher-Porter bottle under $N_2$ atmosphere (15 psia). The bottle was sealed and then immersed in a 60° C.-oil bath and the solution was magnetically stirred for several minutes to dissolve all the solids. The bottle was then pressurized to 20 psig with hydrogen gas ($H_2$). After pressurization, the bottle was sealed off under static hydrogen pressure (valve to hydrogen source was closed) and the solution was stirred for 4 hours (since hydrogen pressurization) at 60° C. At the end of the 4 hours the bottle pressure had decreased to 2 psig and the reaction solution was much more viscous and difficult to stir than at the start of the reaction. The bottle was cooled to room temperature and depressurized, and the solution was analyzed by FID GC. Calculated COD conversion was 8.5 wt. %.

The reaction solution was diluted with heptane. BHT (50 mg) and charcoal (5.5 g, 100-mesh Darco G-60 brand) were added. The solution was stirred at room temperature and the charcoal was then removed by filtration. Solvents and volatiles were removed from the filtrate by rotary evaporation under vacuum (95° C., 0.1–1 mm Hg), affording 1.4 grams of a dark greenish, tacky, gummy solid product. GPC analysis of the product was as follows: $M_n$=134,000, $M_w$=280,000, $M_w/M_n$=2.1 (THF solvent; polystyrene calibration). $^{13}C$ and $^1H$ NMR analyses (as described in Example 21) indicated that the product possessed a non-hydrogenated 1,4-polybutadiene backbone structure with a 75:25 cis/trans carbon-carbon double bond ratio. The analyses indicate that the product was high molecular weight 1,4-polybutadiene, the expected product of ring-opening metathesis polymerization (ROMP) of 1,5-cyclooctadiene. Details are in Table 4.

Example 25

This example illustrates the effect of component (C), the carbon-to-carbon triple bond component of the catalyst system, wherein the alkyne is a terminal alkyne. Conversion of the 1,4-COD increased to 56 wt. % from 8.5 wt. % of Example 24, wherein the alkyne was a non-terminal alkyne.

The alkyne employed was a terminal alkyne, 1-decyne. This example was performed by the procedure of Example 24 except that 1-decyne (0.48 mmol, Aldrich) was employed in place of 3-hexyne in the reaction solution. A stock solution of 1-decyne in chlorobenzene was prepared with a concentration of 0.066 g 1-decyne/mL, and 1.0 mL of this stock solution was employed in the reaction solution. The bottle containing the reaction solution was pressurized to 15 psig with hydrogen. After 45 minutes at 60° C. the viscosity of the solution had increased so greatly that the magnetic stirring had ceased. After 4 hours reaction time at 60° C. the solution was nearly solid in texture and consistency, and the bottle pressure had decreased to 12 psig. The bottle was then cooled to room temperature and depressurized. GC-calculated COD conversion was 56 wt. %.

Solvents and volatiles were removed from the reaction solution by rotary evaporation under vacuum, affording 11.5 grams of a dark-colored, tacky solid product. GPC analysis of the product was as follows: $M_n$=112,000, $M_w$=280,000, $M_w/M_n$=2.5 (THF solvent; polystyrene calibration). $^{13}C$ and $^1H$ NMR analyses (as described in Example 21) indicated that the product possessed a non-hydrogenated 1,4-polybutadiene backbone structure with a 68:32 cis/trans carbon-carbon double bond ratio. The analyses indicate that the product was high molecular weight 1,4-polybutadiene, the expected product of ring-opening metathesis polymerization (ROMP) of 1,5-cyclooctadiene. Details are in Table 4.

Example 26

This example illustrates effect of a substituted non-terminal alkyne as component (C) of the catalyst system, wherein the alkyne is 1,4-diacetoxy-2-butyne. Conversion of the 1,4-COD decreased to 43 wt. % from the 56 wt. % conversion of Example 25.

The alkyne employed was 1,4-diacetoxy-2-butyne. This example was performed by the procedure of Example 24 except that 1,4-diacetoxy-2-butyne (0.48 mmol, Aldrich) was employed in place of 3-hexyne in the reaction solution. A stock solution of 1,4-diacetoxy-2-butyne in chlorobenzene was prepared with a concentration of 0.082 g 1,4-diacetoxy-2-butyne/mL, and 1.0 mL of this stock solution was employed in the reaction solution. The bottle containing the reaction solution was pressurized to 16 psig with hydrogen. After 30 minutes at 60° C. the viscosity of the solution had increased so greatly that the magnetic stirring had ceased. After 3 hours reaction time at 60° C., the solution was rubbery solid in texture and consistency, and the bottle pressure had decreased to 14–15 psig. The bottle was then cooled to room temperature and depressurized. GC-calculated COD conversion was 43%. The polymer product was not isolated. Details are in Table 4.

Example 27

No alkyne was employed. This example demonstrates the need for the alkyne (a component containing a carbon-to-carbon triple bond) catalyst component in order for the catalyst system to effectively catalyze the olefin metathesis reaction.

This example was performed by the procedure of Example 26 except that no alkyne (1,4-diacetoxy-2-butyne) was employed. After 4 hours reaction time at 60° C. the bottle pressure had decreased to 2 psig and no increase in reaction solution viscosity was observed. The bottle was then cooled to room temperature and depressurized. GC-calculated COD conversion was 0%. Details are in Table 4.

TABLE 4

| | Catalyst Components (mmol) | | | Reactants (mmol) | | Reaction Conditions | | Conversion (wt. %) | |
|---|---|---|---|---|---|---|---|---|---|
| Example | A | B | C | 1,4-DAB | 1,5-COD | ° C. | Hrs. | COD | DAB |
| 19 | 0.16 | 0.64 | 0.035 | 23 | 122 | 90 | 3 | 35 | 17 |
| 20 | 0.16 | 0.64 | 0.035 | 23 | 122 | 90 | 3 | 70 | 34 |
| 21 | 0.16 | 0.32 | 0.07 | 47 | 244 | 60 | 4 | 57 | 27 |
| 22 | 0.16 | 0.32 | 0.48 | 47 | 244 | 60 | 4 | 86 | 46 |
| 23 | 0.16 | 0.32 | 0.48 | 47 | 244 | 60 | 4 | 5 | 0 |
| 24 | 0.16 | 0.32 | 0.48 | 0 | 244 | 60 | 4 | 8.5 | — |

TABLE 4-continued

| | Catalyst Components (mmol) | | | Reactants (mmol) | | Reaction Conditions | | Conversion (wt. %) | |
|---|---|---|---|---|---|---|---|---|---|
| Example | A | B | C | 1,4-DAB | 1,5-COD | ° C. | Hrs. | COD | DAB |
| 25 | 0.16 | 0.32 | 0.48 | 0 | 244 | 60 | 4 | 56 | — |
| 26 | 0.16 | 0.32 | 0.48 | 0 | 244 | 60 | 3 | 43 | — |
| 27 | 0.16 | 0.32 | 0 | 0 | 244 | 60 | 4 | 0 | — |

Notes:
Catalyst components in mmol, expressed as compounds
A = Ruthenium constituent
B = Phosphorus constituent
C = Carbon-to-carbon triple bond constituent Examples 28–31

Examples 28–31 were performed according to the procedure of Example 19 except that amount of catalyst component (B), the phosphorus compound, expressed as moles of compound was increased step-wise to illustrate the effect of an increased presence of a phosphorus compound as a component of the catalyst system. All other reaction conditions were as of the procedure which follows.

A solution consisting of 0.049 g [(RuCl$_2$(p-cymene)]$_2$ (0.080 mmol, Strem Chemicals, Inc.), 0.022–0.090 g tricyclohexylphosphine (0.080–0.32 mmol), 0.082 g 1,4-diacetoxy-2-butyne (0.48 mmol, Narchem Corp., 98% purity), 7.4 mL cis-1,4-DAB (47 mmol), 30.0 mL 1,5-COD (244 mmol, 99.9% purity by GC analysis), and 10 mL chlorobenzene solvent was prepared in a 6-oz glass Fisher-Porter bottle under nitrogen atmospheric pressure (15 psia). The bottle was selected and then immersed in a 60° C. oil bath. The solution was magnetically stirred until the solids were dissolved. The bottle was then pressurized to 15–20 psig with hydrogen gas (H$_2$). After pressurization, the bottle was sealed off under static hydrogen pressure (valve to hydrogen source was closed). The solution was stirred for 4 hours after hydrogen pressurization at 60° C. The bottle was then cooled to room temperature and depressurized. The solution was analyzed by FID GC to determine reactant conversion. Details for Examples 28–31 are in Table 5.

Examples 32–33

Examples 32 and 33 were performed to demonstrate the effect of increased hydrogen gas (H$_2$) pressure.

A solution was prepared consisting of [RuCl$_2$(p-cymene)]$_2$, hexylphosphine, 1,4-diacetoxy-2-butyne, and reactants cis-1,4-diacetoxy-2-butene (cis-1,4-DAB) (7.4 mL, 47 mmol) and cis,cis-1,5-cyclooctadiene (1,5-COD) (30.0 mL, 244 mmol), and 10 mL chlorobenzene solvent in a 6-oz glass Fisher-Porter bottle under nitrogen at atmospheric pressure (15 psia). The bottle was sealed and immersed in a 60° C. oil bath. The solution was magnetically stirred to dissolve all the solids. The bottle was then pressurized to desired initial pressure with hydrogen gas (H$_2$). After pressurization, the bottle was sealed off under static hydrogen pressure, the valve to hydrogen source was closed, and the solution was stirred for 4 hours, since hydrogen pressurization, at 60°. The bottle was cooled to room temperature, then depressurized. The solution was analyzed by FID GC to determine reactant conversions.

Details for Examples 32 and 33 are in Table 6.

TABLE 5

| | Catalyst Components | | | | | | Reaction Conditions | | Conversion (wt. %) | |
|---|---|---|---|---|---|---|---|---|---|---|
| | A | | B | | C | | H$_2$ | | | |
| Example | g | mmol | g | mmol | g | mmol | (psig) | ° C. | DAB | COD |
| 28 | 0.049 | 0.080 | 0.022 | 0.080 | 0.082 | 0.48 | 20 | 60 | 3 | 9 |
| 29 | 0.049 | 0.080 | 0.045 | 0.16 | 0.082 | 0.48 | 15 | 60 | 31 | 71 |
| 30 | 0.049 | 0.080 | 0.067 | 0.24 | 0.082 | 0.48 | 18–16 | 60 | 36 | 76 |
| 31 | 0.049 | 0.080 | 0.090 | 0.32 | 0.082 | 0.48 | 18–16 | 60 | 16 | 46 |

Notes:
A = [RuCl$_2$(p-cymene)]$_2$
B = Tricyclohexylphosphine
C = 1,4-diacetoxy-2-butyne

TABLE 6

| Example | Catalyst Components | | | | | | Reaction Conditions | | Conversion (wt. %) | |
|---|---|---|---|---|---|---|---|---|---|---|
| | A | | B | | C | | $H_2$ | | | |
| | g | mmol | g | mmol | g | mmol | (psig) | °C. | DAB | COD |
| 32 | 0.049 | 0.080 | 0.056 | 0.20 | 0.082 | 0.48 | 16 | 60° | 33 | 76 |
| 33 | 0.049 | 0.080 | 0.056 | 0.20 | 0.082 | 0.48 | 50 | 60° | 37 | 78 |

Notes:
A = [RuCl$_2$(p-cymene)]$_2$
B = Tricyclohexylphosphine
C = 1,4-diacetoxy-2-butyne

Examples 34–35

Examples 34 and 35 were performed to demonstrate the effect of increased catalyst component (C), the carbon-to-carbon triple bond component.

The following procedure was employed. A solution was prepared consisting of [RuCl$_2$(p-cymene)]$_2$ (0.098 g, 0.16 mmol), tricyclohexylphosphine (0.090 g, 0.32 mmol), 1,4-diacetoxy-2-butyne (Aldrich), cis-1,4-DAB (7.4 mL, 47 mmol), 1,5-COD (30.0 mL, 244 mmol), and 10 mL chlorobenzene solvent in a 6-oz glass Fisher-Porter bottle under N$_2$ atmosphere (15 psia). The bottle was sealed and then immersed in a 60° C. oil bath and the sodium was magnetically stirred for several minutes to dissolve all the solids. The bottle was then pressurized to 15–20 psig with hydrogen gas (H$_2$). After pressurization, the bottle was sealed off under static hydrogen pressure (valve to hydrogen source was closed) and the solution was stirred for 4 hours (since hydrogen pressurization) at 60° C. The bottle was then cooled to room temperature and depressurized, and the solution was analyzed by FID GC to determine reactant conversions. Reaction data and reactant conversions are given in the following Table 7.

TABLE 7

| Example | Catalyst Components | | | | | | Reaction Conditions | | Conversion (wt. %) | |
|---|---|---|---|---|---|---|---|---|---|---|
| | A | | B | | C | | $H_2$ | | | |
| | g | mmol | g | mmol | g | mmol | (psig) | °C. | DAB | COD |
| 34 | 0.098 | 0.16 | 0.090 | 0.32 | 0.082 | 0.48 | 15 | 60 | 46 | 86 |
| 35 | 0.098 | 0.16 | 0.090 | 0.32 | 0.164 | 0.96 | 15 | 60 | 51 | 92 |

Examples 36–39

The following procedure was employed to demonstrate effect of reaction temperature. A solution was prepared consisting of [RuCl$_2$(p-cymene)]$_2$ (0.049 g, 0.80 mmol), tricyclohexylphosphine (0.056 g, 0.20 mmol), 1,4-diacetoxy-2-butyne (0.082 g, 0.48 mmol - Narchem Corp.), cis-1,4-DAB (7.4 mL, 47 mmol), 1,5-COD (30.0 mL, 244 mmol), and 10 mL chlorobenzene solvent in a 6-oz glass Fisher-Porter bottle under N$_2$ atmosphere (15 psia). The bottle was sealed and then immersed in an oil bath at the desired temperature, and the solution was magnetically stirred for several minutes to dissolve all the solids. The bottle was then pressurized to 15–20 psig with hydrogen gas (H$_2$). After pressurization, the bottle was sealed off under static hydrogen pressure (valve to hydrogen source was closed) and the solution was stirred for 4 hours (since hydrogen pressurization) at the desired reaction temperature (the temperature of the oil bath). The bottle was then cooled to room temperature and depressurized, and the solution was analyzed by FID GC to determine reactant conversions. Reaction data and reactant conversions are given in the following Table 8.

TABLE 8

| Example | Catalyst Components | | | | | | Reaction Conditions | | Conversion (wt. %) | |
|---|---|---|---|---|---|---|---|---|---|---|
| | A | | B | | C | | $H_2$ | | | |
| | g | mmol | g | mmol | g | mmol | (psig) | °C. | DAB | COD |
| 36 | 0.049 | 0.080 | 0.056 | 0.20 | 0.082 | 0.48 | 15 | 45 | 5 | 19 |
| 37 | 0.049 | 0.080 | 0.056 | 0.20 | 0.082 | 0.48 | 16 | 60 | 33 | 76 |
| 38 | 0.049 | 0.080 | 0.056 | 0.20 | 0.082 | 0.48 | 15 | 82 | 51 | 91 |
| 39 | 0.049 | 0.080 | 0.056 | 0.20 | 0.082 | 0.48 | 19 | 90 | 41 | 84 |

Examples 40–43

The following Examples were performed according to the procedure of Example 22, except that different ruthenium compounds (catalyst component A) are employed. These ruthenium compounds are all of the [RuCl$_2$(arene)]$_2$ structure, but employ arenes other than p-cymene.

[RuCl$_2$(arene)]$_2$ compounds were prepared by heating a suspension of [RuCl$_2$(p-cymene)]$_2$ in neat arene.

Example 40

[RuCl$_2$(4-tert-butyltoluene)]$_2$ was prepared by refluxing a suspension of [RuCl$_2$(p-cymene)]$_2$ (3 g, Strem Chemicals) in 100 mL 4-tert-butyltoluene (Aldrich, 95%, b.p. 190° C.) for 2 hours under N$_2$. The solution was cooled. Solids were collected by filtration and washed with heptane. A 2-gram portion of the isolated solids was refluxed in 100 mL fresh 4-tert-butyltoluene for 6 hours under N$_2$. This solution was cooled and the solids were isolated by filtration. The solids were washed with heptane and dried in a vacuum oven at 70° C. Approximately 1.95 grams of red crystals were obtained. $^1$H NMR analysis of this product was consistent with the material being 91% pure [RuCl$_2$(4-tert-butyltoluene)]$_2$ with about 9% unreacted [RuCl$_2$(p-cymene)]$_2$. $^1$H NMR data for [RuCl$_2$(4-tert-butyltoluene)]$_2$ (CDCl$_3$ solvent): δ1.40 (s, 9H), 2.11 (s, 3H), 5.3 (d, 2H), 5.8 (d, 2H).

Example 41

[RuCl$_2$(1,3-diisopropylbenzene)]$_2$ was prepared by stirring a suspension of [RuCl$_2$(p-cymene)]$_2$ (3 g) in 100 mL 1,3-diisopropylbenzene (Aldrich, 96%) for a total of 8 hours at 190° C. under N$_2$. The solution was cooled. Solids were collected by filtration, washed with heptane, and dried in a vacuum oven at 70° C. Approximately 2.6 grams of light brown solid was obtained. $^1$H NMR analysis of this product was consistent with the material being 90+% pure [RuCl$_2$(1,3-diisopropylbenzene)]$_2$ with a small amount of unreacted [RuCl$_2$(p-cymene)]$_2$. $^1$H NMR data for [RuCl$_2$(1,3-diisopropylbenzene)]$_2$ (CDCl$_3$ solvent): δ1.27 (d, 12H), 2.95 (m, 2H), 5.23 (s, 1H), 5.4 (d, 2H), 5.7 (t, 1H).

Example 42

[RuCl$_2$(1,4-diisopropylbenzene)]$_2$ was prepared by stirring a suspension of [RuCl$_2$(p-cymene)]$_2$ (3 g) in 100 mL 1,4-diisopropylbenzene (Aldrich, 97%) for 8 hours at 190° C. under N$_2$. The solution was cooled. Solids were collected by filtration, washed with heptane, and dried in a vacuum oven at 70° C. Approximately 2.95 grams of red solid was obtained. A 2.6-gram portion of the red solid was stirred at 190° C. in 100 mL fresh 1,4-diisopropylbenzene for 6 hours. After cooling, solids were collected by filtration, washed with heptane, and dried in a vacuum oven at 70° C. A red-brown solid product was obtained (2.5 grams). $^1$H NMR analysis of this product was consistent with the material being 90+% pure [RuCl$_2$(1,4-diisopropylbenzene)]$_2$ with a small amount of unreacted [RuCl$_2$(p-cymene)]$_2$. $^1$H NMR data for [RuCl$_2$(1,4-diisopropylbenzene)]$_2$ (CDCl$_3$ solvent): δ1.28 (d, 12H), 2.9 (m, 2H), 5.45 (s, 4H).

Example 43

[RuCl$_2$(1,3,5-triisopropylbenzene)]$_2$ was prepared by stirring a suspension of [RuCl$_2$(p-cymene)]$_2$ (3 g) in 120 mL 1,3,5-triisopropylbenzene (Aldrich, 97%) for a total of 8 hours at 190° C. under N$_2$. The solution was cooled to room temperature and then placed in a refrigerator for 2–3 days. Solids were collected by cold filtration, washed with heptane, and dried in a vacuum oven at 70° C. A red-brown solid product was obtained (3.25 grams). $^1$H NMR analysis of this product was consistent with the material being 90+% pure [RuCl$_2$(1,3,5-triisopropylbenzene)]$_2$ with a small amount of unreacted [RuCl$_2$(p-cymene)]$_2$. $^1$H NMR data for [RuCl$_2$(1,3,5-triisopropylbenzene)]$_2$ (CDCl$_3$ solvent): δ1.3 (d, 18H), 3.1 (m, 3H), 5.2 (s, 3H).

The following procedure given was employed for the olefin metathesis reaction of 1,5-COD and cis-1,4-DAB.

A solution was prepared consisting of [RuCl$_2$(arene)]$_2$ (0.040 mmol), tricyclohexylphosphine (0.028 g, 0.10 mmol), 1,4-diacetoxy-2-butyne (0.041 g, 0.24 mmol), cis-1,4-DAB (7.4 mL, 47 mmol), 1,5-COD (30.0 mL, 244 mmol), and 10 mL chlorobenzene solvent in a 6-oz glass Fisher-Porter bottle under N$_2$ atmosphere (15 psia). The bottle was sealed and then immersed in a 60° C.-oil bath and the solution was magnetically stirred for several minutes to dissolve all the solids. The bottle was then pressurized to 15–17 psig with hydrogen gas (H$_2$). After pressurization, the bottle was sealed off under static hydrogen pressure (valve to hydrogen source was closed) and the solution was stirred for 4 hours (since hydrogen pressurization) at 60° C. The bottle was then cooled to room temperature and depressurized, and the solution was analyzed by FID GC to determine reactant conversions. Reaction data and reactant conversions are given in the following table:

TABLE 9

| | | Catalyst Components | | | | | | Reaction Conditions | | Conversion | |
|---|---|---|---|---|---|---|---|---|---|---|---|
| | Arene in Catalyst | A | | B | | C | | H$_2$ | | (wt. %) | |
| Example | Component A | g | mmol | g | mmol | g | mmol | (psig) | °C. | DAB | COD |
| 40 | 4-tert-Butyltoluene | 0.026 | 0.040 | 0.028 | 0.10 | 0.041 | 0.24 | 15–17 | 60 | 32 | 71 |
| 41 | 1,3-Diisopropylbenzene | 0.027 | 0.040 | 0.028 | 0.10 | 0.041 | 0.24 | 15–17 | 60 | 7 | 34 |
| 42 | 1,4-Diisopropylbenzene | 0.027 | 0.040 | 0.028 | 0.10 | 0.041 | 0.24 | 15–17 | 60 | 22 | 60 |
| 43 | 1,3,5-Triisopropylbenzene | 0.030 | 0.040 | 0.028 | 0.10 | 0.041 | 0.24 | 15–17 | 60 | 28 | 67 |

Notes:
A = [RuCl$_2$(p-arene)]$_2$
B = Tricyclohexylphosphine
C = 1,4-diacetoxy-2-butyn From the foregoing, further variations and modifications of this invention will be apparent to those skilled in the art and are intended to be encompassed by the claims appended hereto.

What is claimed is:

1. A ruthenium-containing olefin metathesis catalyst system comprising a ruthenium compound (A), a phosphorus, arsenic or antimony compound (B), and a compound (C) containing at least one carbon-to-carbon triple bond, wherein mole ratios of compounds A:B:C are in the range of about 1.0:0.01–100:0.01–500, wherein the ruthenium compound (A) is selected from the group consisting of $RuX_3$, $RuX_3$.hydrate, $[RuCl_2(p\text{-cymene})]_2$, $[RuCl_2(4\text{-tert-butyltoluene})]_2$, $[RuCl_2(1,3\text{-diisopropylbenzene})]_2$, $[RuCl_2(1,4\text{-diisopropylbenzene})]_2$, and $[RuCl_2(1,3,5\text{-triisopropylbenzene})]_2$ wherein X is a halogen, and wherein hydrogen is present as a catalyst system activator at a partial pressure of hydrogen of from $1\times10^{-2}$ mm Hg to about 200 atmospheres.

2. The ruthenium-containing catalyst system of claim 1, wherein the compound (B) has the formula $ER'_3$ wherein E is phosphorus, arsenic or antimony and wherein R' is selected from R and (OR) wherein each of the R groups are the same or different and are each selected from the group consisting of hydrogen, halogen, alkyl, cycloalkyl, aryl and arylalkyl groups unsubstituted or substituted, wherein each alkyl, cycloalkyl, aryl and arylalkyl group contains up to about 20 carbon atoms, wherein each substituent may be the same or different and is selected from the group consisting of halogen and alkyl and aryl groups containing up to about 20 carbon atoms and wherein if R' is OR, then R' and R are not hydrogen or halogen, and if R' is R then at least one R is not hydrogen or halogen.

3. The ruthenium-containing catalyst of claim 2 wherein E is phosphorus.

4. The ruthenium-containing catalyst system of claim 1, wherein the compound (B) is selected from the group consisting of phosphine compounds and phosphite compounds of the formulae $PR_3$, $P(OR)_3$, $PH_2R$, $PHRR^1$, $PRR'R^2$, and $P(OR)(OR')(OR^2)$, wherein P is phosphorus and wherein R, $R^1$ and $R^2$ are the same or different and are each selected from the group consisting of unsubstituted and substituted alkyl, cycloalkyl, aryl and arylalkyl groups of up to about 20 carbon atoms.

5. The ruthenium-containing catalyst system of claim 1, wherein the compound (B) is selected from the group consisting of arsenic and antimony compounds of the formulae $ER_3$, $EH_2R$, $EHRR^1$, and $ERR^1R^2$, wherein E is arsenic or antimony, and wherein R, $R^1$ and $R^2$ are the same or different and are each selected from the group consisting of unsubstituted and substituted alkyl and aryl groups of up to about 20 carbon atoms.

6. The ruthenium-containing catalyst system of claim 1, wherein the compound (C) is a substituted or unsubstituted alkyne containing up to about 20 carbon atoms.

7. The ruthenium-containing catalyst system of claim 1, wherein the compound (C) is selected from the group consisting of a terminal alkyne, an internal alkyne, an alkyne possessing one or more aliphatic, alkenyl, aromatic, halogen, ester, hydroxyl, ketone, aldehyde, ether, carboxyl, amide, anhydride, nitrile, silyl or amine groups, and mixtures thereof.

8. The ruthenium-containing catalyst system of claim 1, wherein compound (B) is tricyclohexylphosphine, and said compound containing a carbon-to-carbon triple bond (C) is selected from the group consisting of 1,4-diacetoxy-2-butyne, 3-hexyne, and 1-decyne.

* * * * *

UNITED STATES PATENT AND TRADEMARK OFFICE
CERTIFICATE OF CORRECTION

PATENT NO. : 6,159,890
DATED : December 12, 2000
INVENTOR(S) : Philip O. Nubel, Craig Lane Hunt, David S. Choi, Tobin J. Marks It is certified that error appears in the above-identified patent and that said Letters Patent is hereby corrected as shown below:

Title page,
ABSTRACT, "ligand. Hydrogen gas is used as an activator. A process for" should read -- ligand. A process for --

Column 4,
Line 50, "$(OR^2)$], atoms, preferably" should read -- $(OR^2)$], is an aromatic ligand of up to about 30 carbon atoms, preferably --

Column 5,
Lines 41 and 42, "$DR_3$, $DH_2R$, $ER_3$, $EH_2R$, $EHRR^1$, and $ERR^1R^2$" should read -- $ER_3$, $EH_2R$, $EHRR^1$, and $ERR^1R^2$ --

Column 19,
Line 14, "ratio and that end groups was" should read -- ratio and that the proportion of chain end groups was --

Column 24,
Line 25, "hexylphosphine," should read -- tricyclohexylphosphine, --

Signed and Sealed this

Eighteenth Day of December, 2001

Attest:

*Attesting Officer*

JAMES E. ROGAN
*Director of the United States Patent and Trademark Office*